(12) United States Patent
Hiraoka et al.

(10) Patent No.: US 7,335,757 B2
(45) Date of Patent: Feb. 26, 2008

(54) CARBONYL REDUCTASE, GENE ENCODING THE SAME, AND PROCESS FOR PRODUCING OPTICALLY ACTIVE ALCOHOLS USING THE SAME

(75) Inventors: Hirotoshi Hiraoka, Kanagawa (JP); Makoto Ueda, Kanagawa (JP); Mari Hara, Kanagawa (JP)

(73) Assignees: Mitsubishi Chemical Corporation, Tokyo (JP); Nissan Chemical Industries, Ltd., Tokyo (JP)

( * ) Notice: Subject to any disclaimer, the term of this patent is extended or adjusted under 35 U.S.C. 154(b) by 199 days.

(21) Appl. No.: 10/943,202

(22) Filed: Sep. 17, 2004

(65) Prior Publication Data

US 2005/0048633 A1    Mar. 3, 2005

Related U.S. Application Data

(63) Continuation-in-part of application No. PCT/JP03/03262, filed on Mar. 18, 2003.

(30) Foreign Application Priority Data

Mar. 19, 2002   (JP)   ............................. 2002-075921

(51) Int. Cl.
*C07H 21/04* (2006.01)
*C07K 1/00* (2006.01)

(52) U.S. Cl. .................. 536/23.2; 536/23.1; 530/350; 530/370; 530/371

(58) Field of Classification Search ............ None
See application file for complete search history.

(56) References Cited

U.S. PATENT DOCUMENTS

| 5,011,930 A | 4/1991 | Fujikawa et al. ............ 546/101 |
| 2004/0030139 A1 | 2/2004 | Hara et al. .................. 546/174 |

FOREIGN PATENT DOCUMENTS

| EP | 304063 | 2/1989 |
| JP | 08-092217 | 4/1996 |
| JP | 08-127585 | 5/1996 |
| WO | 02/063028 | 8/2002 |

OTHER PUBLICATIONS

Miller et al. ("Genetic variability in susceptibility and response to toxicants" Toxicol Lett. Mar. 31, 2001;120(1-3):269-80.*
Yamaguchi et al. ("Murine DNA polymerase beta gene: mapping of transcription initiation sites and the nucleotide sequence of the putative promoter region" Mol Cell Biol. May 1987;7(5):2012-8).*
GenBank accession No. M16363.*
SCORE printout.*
Yamada et al. ("The phylogenetic relationships of the hat-shaped ascospore-forming, nitrate-assimilating *Pichia* species, formerly classified in the genus *Hansenula* Sydow et Sydow, based on the partial sequences of 18S and 26S ribosomal RNAs (*Saccharomycetaceae*): the proposals of three new genera, *Ogataea, Kuraishia*, and *Nakazawaea*" Biosci Biotechno.*
Yamada et al. ("The Molecular Phylogeny of the Q8-Equipped Basidiomycetous Yeast Genera Mrakia Yamada et Komgata and Cystofilobastidium Oberwinkler et Badoni Based on the Partial Sequences of 18S and 26S Ribosomal Ribonucleic Acids" J. Gen. Appl. Microbiol. 1989; 35:173-183).*
Yamada et al. ("The phylogenetic relationships of the hat-shaped ascospore-forming, nitrate-assimilating *Pichia* species, formerly classified in the genus *Hansenula* Sydow et Sydow, based on the partial sequences of 18S and 26S ribosomal RNAs (*Saccharomycetaceae*): the proposals of three new genera, *Ogataea, Kuraishia*, and *Nakazawaea*" Biosci Biotechno, 1994.*
GenBank accession No. M16363, Apr. 1993.*
M. Kataoka et al., "Novel bioreduction system for the production of chiral alcohols", Appln. Microbiol Biotechnol, vol. 62, pp. 437-455, 2003.

* cited by examiner

*Primary Examiner*—Kenneth R. Horlick
*Assistant Examiner*—Christopher M. Babic
(74) *Attorney, Agent, or Firm*—Wenderoth, Lind & Ponack, L.L.P.

(57) ABSTRACT

According to the present invention, there is provided a novel carbonyl reductase derived from a microbial belonging to the genus *Ogataea* and a DNA encoding the enzyme. By reducing ketones with the use of the carbonyl reductase, optically active alcohols, in particular, (E)-7-[2-cyclopropyl-4-(4-fluorophenyl)-quinolin-3-yl]-3,5-dihydroxy-hept-6-enoic acid esters can be produced. The carbonyl reductase according to the present invention is excellent in activity and stereoselectivity. Thus, according to the present invention, there is provided a process for producing optically active alcohols, which are industrially useful as intermediate materials for drugs, pesticides, etc.

4 Claims, No Drawings

CARBONYL REDUCTASE, GENE ENCODING THE SAME, AND PROCESS FOR PRODUCING OPTICALLY ACTIVE ALCOHOLS USING THE SAME

This application is a continuation-in-part of International Application No. PCT/JP03/03262 filed Mar. 18, 2003.

TECHNICAL FIELD

The present invention relates to: a polypeptide having an activity to reduce carbonyl group-containing compounds to convert them to optically active alcohols that are industrially useful compounds as intermediate materials for drugs, pesticides, and the like; a DNA encoding the polypeptide; a recombinant DNA obtained by incorporating the DNA into a vector; and a transformant having the recombinant DNA. Further, the present invention relates to a process for producing optically active alcohols using the transformant, culture of the transformant, or a treated product of the transformant.

BACKGROUND ART

As a method of chemically producing (E)-7-[2-cyclopropyl-4-(4-fluorophenyl)-quinolin-3-yl]-3,5-dihydroxy-hept-6-enoic acid esters, for example, the following production route has been known as disclosed in Patent Document 1.

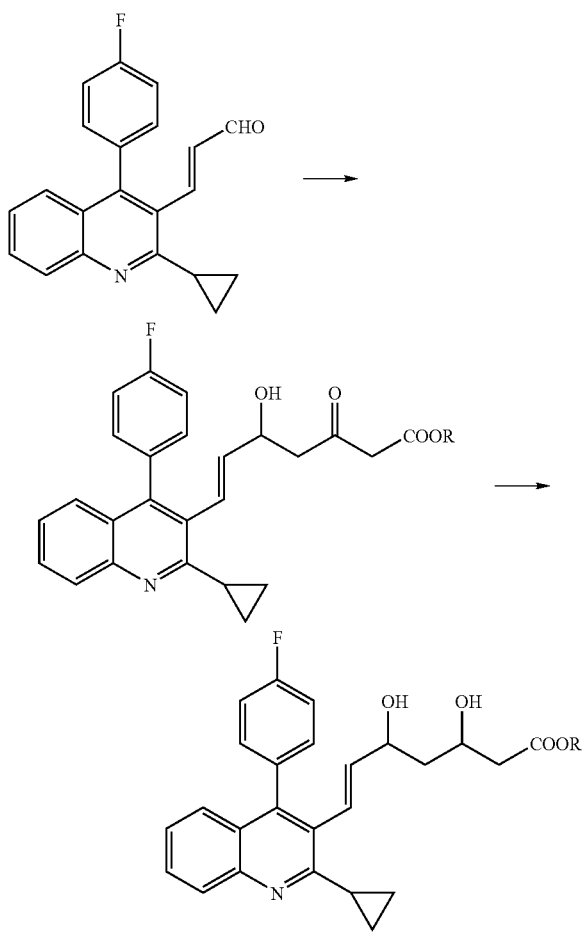

Furthermore, Patent Document 2 discloses another production process using an optically active Schiff base.

Still furthermore, Patent Document 3 discloses a production process using methyl (R)-3-tert-butyl dimethylsilyloxy-6-dimethoxyphosphinyl-5-oxohexanoate at a very low temperature.

On the other hand, a method of producing an optically active alcohol product by a stereo-selective reduction of a compound having a carbonyl group using microbial cells and/or a cell preparation is applicable as a cost effective method of production with few byproducts to the manufacturing of the above compound. As a method for a compound including a quinolin ring in a side chain of a carbonyl group, Non-Patent Document 1 has described that the following reaction can be performed using *Microbacterium campoquemadoensis*

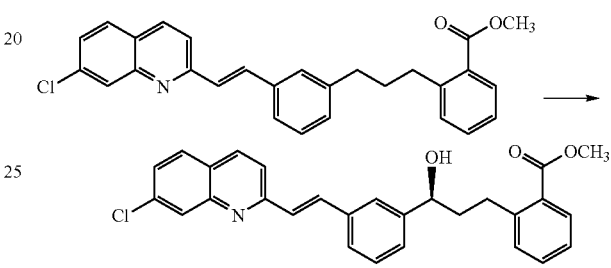

Furthermore, Non-Patent Document 2 has a description that the following reaction can be performed using a bakers yeast.

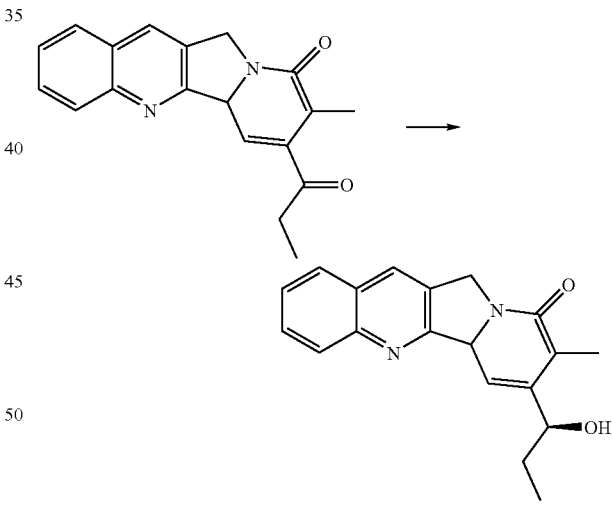

However, with respect to a compound in which carbonyl groups continuously exist in the molecule thereof in addition to the presence of olefin on the α-position of the carbonyl groups, such as (E)-7-[2-cyclopropyl-4-(4-fluorophenyl)-quinolin-3-yl]-3,5-dioxohepto-6-enoic acid esters, no example in which such a compound can be reduced using a microorganism in a stereo-selective manner has been known in the art.

<Non-Patent Document 1> Appl microbial Biotechnol (1998) 49: p. 709-717

<Non-Patent Document 2> Bioorg Med Chem Lett, vol. 8, p. 1403-(1998)

<Patent Document 1> JP 1-279866 A
<Patent Document 2> JP 8-92217 A
<Patent Document 3> JP 8-127585 A

DISCLOSURE OF THE INVENTION

Therefore, it has been desired to develop a novel production process with which (3R,5S)-(E)-7-[2-cyclopropyl-4-(4-fluorophenyl]-quinolin-3-yl]-3,5-dihydroxyhept-6-enoic acid esters can be cost-effectively produced on an industrial scale.

To solve the above-mentioned problems, the inventors of the present invention have made intensive studies on a process for producing (3R,5S)-(E)-7-[2-cyclopropyl-4-(4-fluorophenyl)-quinolin-3-yl]-3,5-dihydroxyhept-6-enoic acid esters. As a result, they have found that an objective compound can be obtained with a high optical purity and a high concentration by: isolating a novel enzyme that catalyzes a reduction reaction of carbonyl group-containing compounds that can be used as starting materials; and allowing the enzyme, which is expressed by using a recombinant bacteria, to act on the carbonyl group-containing compounds that can be used as starting materials. Thus, they have achieved the present invention.

That is, the gist of the present invention resides in:

(1) A polypeptide, comprising an amino acid sequence of (A) or (B) below:

(A) an amino acid sequence described in SEQ ID NO: 1; and (B) an amino acid sequence of a polypeptide having a carbonyl reductase activity, the amino acid sequence is an amino acid sequence including deletion, addition, or substitution of one or a plurality of amino acids in the amino acid sequence described in SEQ ID NO: 1.

(2) A DNA, comprising a nucleotide sequence of any one of (a) to (e) below:

(a) a nucleotide sequence encoding a polypeptide consisting of an amino acid sequence described in SEQ ID NO: 1;

(b) a nucleotide sequence encoding a polypeptide having a carbonyl reductase activity, the polypeptide consists of an amino acid sequence including deletion, addition, or substitution of one or a plurality of amino acids in the amino acid sequence described in SEQ ID NO:1;

(c) a nucleotide sequence described in SEQ ID NO: 2;

(d) a nucleotide sequence encoding a polypeptide having a carbonyl reductase activity, the nucleotide sequence is a nucleotide sequence including deletion, addition, or substitution of one or a plurality of bases in the nucleotide sequence described in SEQ ID NO:2; and (e) a nucleotide sequence that hybridizes with the nucleotide sequence described in SEQ ID NO:2 or a complementary nucleotide sequence thereof or a part of these sequences under stringent conditions, the nucleotide sequence encoding a polypeptide having a carbonyl reductase activity.

(3) A recombinant DNA obtained by incorporating a DNA according to (2) into a vector.

(4) A transformant having a recombinant DNA according to (3).

(5) A transformant obtained by incorporating a DNA according to (2) into a chromosomal DNA.

(6) A process for producing a compound represented by the following formula (IV)

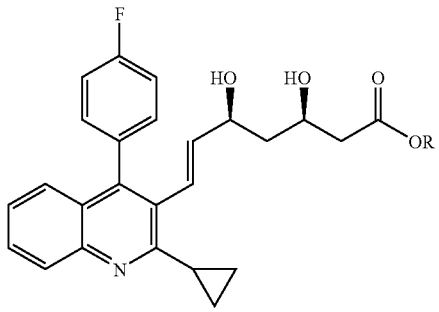

(where R represents a hydrogen atom, an alkyl group, or an aryl group), comprising:

reacting a carbonyl group-containing compound selected from the group consisting of a compound represented by the following formula (I)

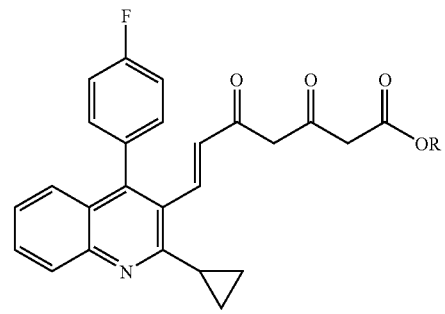

(where R has the same meaning as that described above), a compound represented by the following formula (II)

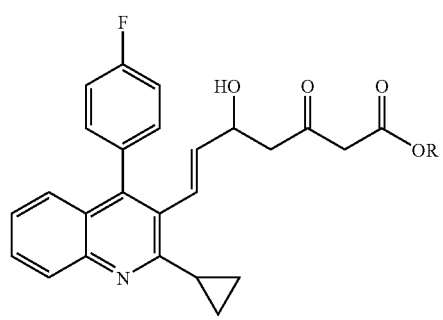

(where R has the same meaning as that described above), and a compound represented by the following formula (III)

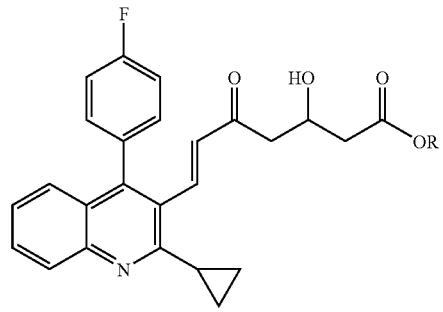

III (where R has the same meaning as that described above) with any one selected from the group consisting of a transformant cell according to (4) or (5), a culture broth of the transformant cell, and a treated product of the transformant cell to asymmetrically reduce the carbonyl group-containing compound.

(7) A process according to (6), wherein the compounds represented by formulae (II) and (III) consist of optically active forms represented by the following formula (II')

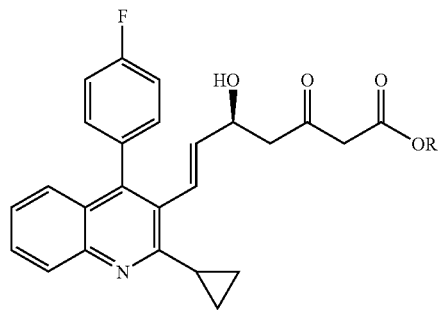

II'

(where R has the same meaning as that described above) and the following formula (III')

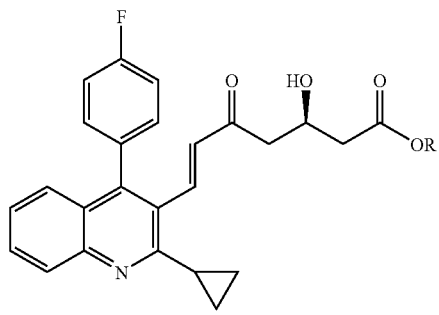

III'

(where R has the same meaning as that described above), respectively.

(8) A process for producing a compound represented by the following formula (V),

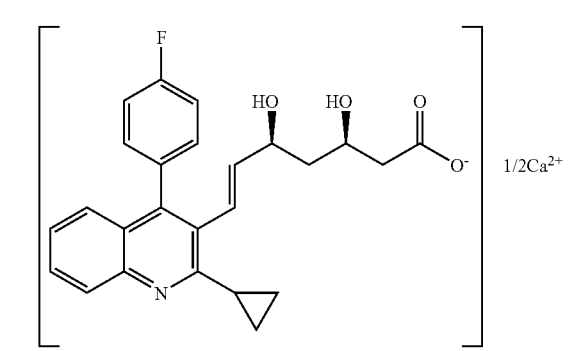

V comprising:

reacting a carbonyl group-containing compound selected from the group consisting of a compound represented by the following formul (I)

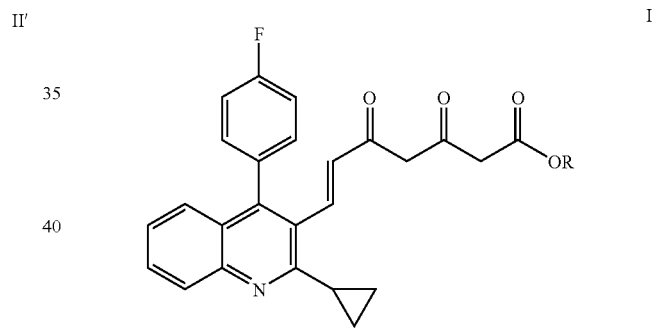

I (where R represents a hydrogen atom, an alkyl group, or an aryl group), a compound represented by the following formula (II)

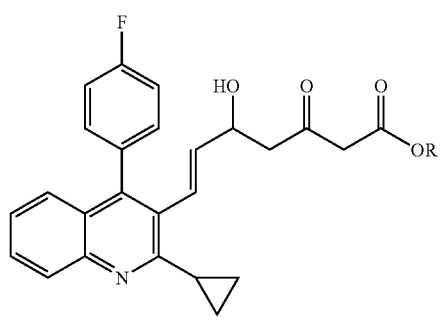

II (where R has the same meaning as that described above), and a compound represented by the following formula (III)

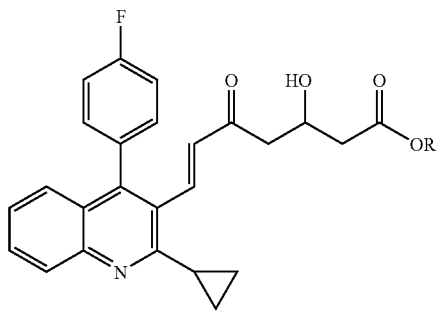

( where R has the same meaning as that described above) with any one selected from the group consisting of a transformant cell according to (4) or (5), a culture broth of the transformant cell, and a treated product of the transformant cell to obtain a compound represented by the following formula (IV)

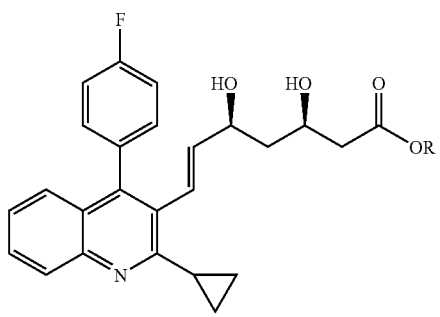

(where R has the same meaning as that described above) by asymmetrically reducing the carbonyl group-containing compound; and deesterifying the obtained compound represented by the formula (IV), and reacting a divalent calcium ion with the compound represented by the formula (IV) to form the calcium salt thereof.

(9) A process according to (8), wherein the compounds represented by formulae (II) and (III) consist of optically active forms represented by the following formula (II')

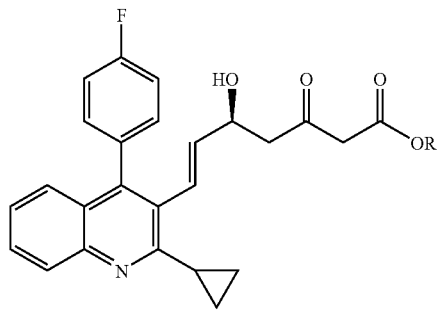

(where R has the same meaning as that described above) and the following formula (III')

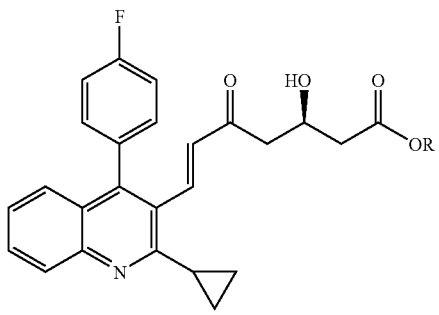

(where R has the same meaning as that described above), respectively.

BEST MODE FOR CARRYING OUT THE INVENTION

Hereinafter, the present invention will be described in detail.

The polypeptide of the present invention is one having the amino acid sequence described in SEQ ID NO: 1 or a homolog thereof having a carbonyl reductase activity.

The "carbonyl reductase activity" as used herein refers to activity that asymmetrically reduces carbonyl groups in carbonyl group-containing compounds to produce optically active alcohols. Such an activity can be measured by: reacting an objective polypeptide, a transformant, culture of the transformant, or treated product of the transformant as an enzyme in a reaction system containing a carbonyl group-containing compound as a substrate and NADPH as a coenzyme; and measuring an initial rate of decrease in NADPH.

Since its amino acid sequence and nucleotide sequence encoding the amino acid sequence have been elucidated by the present invention, the polypeptide of the present invention can be obtained by: isolating DNA encoding a reductase from any microorganism having a carbonyl group reducing activity by use of a probe prepared based on a nucleotide sequence that encodes a partial or whole amino acid sequence of the polypeptide of the present invention; and then using a conventional gene engineering technique based on the isolated DNA, as will be described hereinbelow. Further, as has been made upon completion of the present invention, the polypeptide of the present invention can be purified from culture broths of microorganisms having a carbonyl group reducing activity, that is, microorganisms having DNA that encodes a carbonyl reductase, for example, yeasts belonging to the genus *Ogataea*.

Among the yeasts that belong to the genus *Ogataea*, for example, *Ogataea minuta* has particularly excellent productivity of the carbonyl reductase of the present invention. The yeast is available from Institute for Fermentation, Osaka as IFO 1473 strain.

Any conventional purification method can be used as a method of obtaining the polypeptide of the present invention from the culture broths of microorganisms. For example, the following method can be used. After the above-mentioned microorganism has been sufficiently proliferated by cultivating it in a common medium for use in cultivation of fungi, such as YM medium, the microorganism is collected and disrupted in a buffer, which is added with a reducing agent such as DTT (dithiothreitol) or a protease inhibitor such as phenylmethanesulfonyl fluoride (PMSF), to form a cell-free extract. The polypeptide can be purified from the cell-free extract by appropriate combinations of fractionation based on solubility of a protein (such as precipitation with organic solvents, or salting out with ammonium sulfate or the like), cation exchange, anion exchange, gel filtration, hydrophobic chromatography, affinity chromatography with chelate, dye-stuff, antibody, or the like, and so on. For example, the polypeptide can be purified to almost an electrophoretically single band through anion exchange chromatography using DEAE-Sepharose, hydrophobic chromatography using octyl-Sepharose, anion exchange chromatography using Q-Sepharose, gel filtration using Superdex 200, or the like.

The thus-purified polypeptide of the present invention derived from *Ogataea minuta* typically has the following properties.

(1) Optimum pH
  5.0 to 6.0.

(2) Molecular Weight
  About 27,000 Da by measurement of molecular weight by sodium dodecylsulfate-polyacrylamide gel electrophoresis (hereinafter, abbreviated as "SDS-PAGE").

Further the enzyme can be characterized by the following properties.

(3) Stable pH Range
  Relatively stable in the range of pH 5.5 to 6.5.

(4) Operation Temperature Range
  Optimum temperature is 60 to 70° C.

(5) Temperature Stability
  Relatively stable up to 40° C.

(6) Inhibition
  The enzyme is inhibited by a mercury (I) ion and a lead (II) ion.

The polypeptide of the present invention isolated by the above-mentioned method is an excellent enzyme that has an ability to asymmetrically reduce not only carbonyl group-containing compounds but also dicarbonyl compounds.

A homolog of the polypeptide of the present invention refers to a polypeptide, comprising an amino acid sequence including deletion, addition, or substitution of one or a plurality of amino acids in the amino sequence described in SEQ ID NO: 1 so far as the carbonyl reductase activity is not deteriorated. The term "a plurality of" as used herein means specifically 20 or less, preferably 10 or less, more preferably 5 or less.

The homolog of the polypeptide of the present invention refers to a polypeptide comprising an amino acid sequence that has at least 50%, preferably at least 60% or 70%, more preferably 80% or more homology to the amino acid sequence described in SEQ ID NO: 1.

Incidentally, homology search of the above-mentioned polypeptide can be performed by searching DNA Databank of JAPAN (DDBJ) using FASTA program or BLAST program. Search of the amino acid sequence described in SEQ ID NO: 1 on DDBJ using Blast program indicated that among the known proteins, the one that showed the highest homology was the probable short chain dehydrogenase (T41540) of *Schizosaccharomyces pombe*, which showed 37.4% homology.

A DNA of the present invention is a DNA that encodes the above-mentioned polypeptide or a homolog thereof having carbonyl reductase activities.

Specific examples of the DNAs that encode the above-mentioned polypeptide include those DNAs that include the nucleotide sequence described in SEQ ID NO: 2.

The DNA that encodes the polypeptide of the present invention can be isolated by, for example, the following method.

First, the polypeptide of the present invention is purified by the above-mentioned method or the like, and then the N-terminal amino acid sequence thereof is analyzed. Further, after the polypeptide has been cleaved with an enzyme such as lysylendopeptidase or V8 protease, the resultant peptide fragments are purified by reversed-phase liquid chromatography or the like. Then, the amino acid sequences of the fragments are analyzed by using a protein sequencer to determine a plurality of amino acid sequences.

Primers for PCR are designed based on the determined amino acid sequences and PCR is performed using chromosomal DNA or cDNA library of a carbonyl reductase producing microbial strain as a template and the PCR primer designed from the determined amino acid sequence to obtain a part of the DNA of the present invention. Further, the DNA of the present invention can be obtained by colony hybridization, plaque hybridization, or the like by using the thus-obtained DNA fragment as a probe and utilizing a library, which is obtained by introducing the chromosomal DNA of the carbonyl reductase producing microbial strain digested with a restriction enzyme into phage, plasmid, or the like or a cDNA library. Further, the DNAs of the present invention can also be obtained by reverse PCR (Genetics 120, 621-623(1988)) including: analyzing the nucleotide sequence of the DNA fragment obtained by PCR; designing a PCR primer for elongating a chain outward from the DNA based on the obtained sequence; and digesting the chromosomal DNA of the carbonyl reductase producing microbial strain with an appropriate restriction enzyme and utilizing an autocyclized DNA as a template, or by an RACE method (Rapid Amplification of cDNA End, "PCR Experiment Manual", p25-33, HBJ Publishing Section), or the like.

Note that since their nucleotide sequences have been elucidated by the present invention, the DNAs of the present invention can be obtained not only by the above-mentioned cloning method as the genome DNA or cDNA, but by chemical synthesis or the like based on SEQ ID NO: 2.

The DNA homologs encoding the polypeptide of the present invention include those DNAs that encode polypeptides comprising an amino acid including deletion, addition, or substitution of one or a plurality of amino acids in the amino sequence described in SEQ ID NO: 1 so far as the carbonyl reductase activity is not deteriorated. Specifically, the DNA homologs encoding the above-mentioned polypeptide include those DNAs having nucleotide sequences that encode polypeptides corresponding to the polypeptide encoded by the nucleotide sequence described in SEQ ID NO: 2 and include deletion, addition, or substitution of one or a plurality of amino acids so far as the carbonyl reductase activity thereof is not deteriorated. The term "a plurality of" as used herein means specifically 60 or less, preferably 30 or less, more preferably 10 or less.

One skilled in the art can obtain the homologs of DNA of the present invention by introducing appropriate substitution, deletion, insertion, and/or addition mutations into the DNA described in SEQ ID NO: 2 by using a site-specific mutation introducing method (Nucleic Acid Res. 10, pp. 6487 (1982), Methods in Enzymol. 100, pp. 448 (1983), Molecular Cloning 2nd Edt., Cold Spring Harbor Laboratory Press (1989), and PCR A Practical Approach IRL Press pp. 200 (1991)), and the like.

Further, the homologs of DNA of the present invention can also be obtained by performing hybridization with DNA prepared from any microorganism having a carbonyl group reducing activity by a colony hybridization method, a plaque hybridization method, a Southern blot hybridization method, or the like using the DNA encoding the polypeptide of the present invention or a part thereof as a probe under stringent conditions to select a DNA that hybridizes with the probe. The term "a part" of DNA that encodes the polypeptide of the present invention means a DNA that has a sufficient length to be used as a probe, specifically, 15 bp or more, preferably 50 bp or more, more preferably 100 bp or more.

Each hybridization may be preformed according to the method described in Molecular Cloning: A Laboratory Manual, 2nd Ed., Cold Spring Harbor Laboratory, Cold Spring Harbor, N.Y., 1989 (hereinafter, abbreviated as "Molecular Cloning, 2nd Ed.") or the like.

The term "nucleotide sequence that hybridizes under stringent conditions" means a nucleotide sequence of a DNA that is obtained by using a colony hybridization method, a plaque hybridization method, a Southern blot hybridization method, or the like using a DNA as a probe under stringent conditions. Examples of the stringent conditions include those conditions in which in the colony hybridization method or plaque hybridization method, hybridization is performed using a filter having fixed thereon a DNA derived from a colony or plaque or a fragment of the DNA in the presence of 0.7 to 1.0 M sodium chloride at 65° C., and then the filter is washed with 0.1 to 2×SSC solution (the composition of 1×SSC is 150 mM sodium chloride and 15 mM sodium citrate) under the condition of 65° C.

Carbonyl reductase expression vectors can be provided by incorporating the thus-isolated DNA that encodes the polypeptide of the present invention into known expression vectors as enable the DNA to express. Further, cultivation of transformants that are transformed with the expression vectors enables one to obtain carbonyl reductase from the transformants. The expression vectors are not particularly limited so far as they can express the DNAs of the present invention and can be selected as appropriate depending on the kind of host microbial to be transformed and the like. Alternatively, the transformants can also be obtained by incorporating the DNA of the present invention to a chromosomal DNA of a known host microbial as enable the DNA to express.

Specific examples of the method of making the transformants include: a method involving introducing the DNA of the present invention into a plasmid vector or phage vector that exists in a microbial stably and introducing the constructed expression vector into the microbial; and a method involving introducing the DNA of the present invention into a host genome directly to allow genetic information thereof to be transcribed and translated.

In the case where the DNA of the present invention does not contain a promoter that can be expressed in a host microbial, an appropriate promoter can be incorporated in the upstream of the 5'-terminal of the DNA chain of the present invention or more preferably, a terminator can be incorporated in the downstream of the 3'-terminal of the DNA chain of the present invention. The promoter and terminator are not particularly limited so far as they are a promoter and a terminator that are known to function in the microbial utilized as a host. Such vectors, promoters, and terminators that can be used in various microbials are described in detail in, for example, "Microbiology Fundamental Course 8, Gene Engineering, Kyoritsu Publishing". In particular, yeasts are described in detail in Adv. Biochem. Eng. 43, 75-102 (1990), Yeast 8, 423-488 (1992) and the like.

The host microbial as a target of transformation for expressing the carbonyl reductase of the present invention is not particularly limited so far as the host itself gives no adverse influence on the reaction. Specific examples thereof include microbials as shown below.

Bacteria that belong to the genera *Escherichia, Bacillus, Pseudomonas, Serratia, Brevibacterium, Corynebacterium, Streptococcus, Lactobacillus*, and so on and of which host vector systems are established;

Actinomycetes that belong to the genera *Rhodococcus, Streptomyces*, and so on and of which host vector systems are established;

Yeasts that belong to the genera *Saccharomyces, Kluyveromyces, Schizosaccharomyces, Zygosaccharomyces, Yarrowia, Trichosporon, Rhodosporidium, Hansenula, Pichia, Candida*, and so on and of which host vector systems are established; and Molds that belong to the genera *Neurospora, Aspergillus, Cephalosporium, Trichoderma*, and so on and of which host vector systems are established.

Among the above-mentioned microbials, preferable hosts include *Escherichia, Bacillus, Brevibacterium*, and *Corynebacterium*, particularly preferably *Escherichia* and *Corynebacterium*.

Procedures for making transformants, construction of recombinant vectors suitable for hosts, and cultivation of hosts can be performed according to the technologies commonly used in the fields of molecular biology, biotechnology, and gene engineering (for example, Sambrook et al., Molecular Cloning, Cold Spring Harbor Laboratories).

Hereinafter, specific examples of host microbial, preferable transforming techniques, vector, promoter, terminator, and so on for each microbial will be described. However, the present invention should not be considered to be limited thereto.

In the case of *Escherichia*, particularly *Escherichia coli*, plasmid vectors include pBR, pUC plasmids, and promoters derived from lac (β-galactosidase), trp (tryptophan operon), tac, trc (fusion of lac and trp), and λ-phage PL and PR. Further, the terminators include trpA derived terminator, phage derived terminator, and rrnB ribosomal RNA derived terminator.

In the case of *Bacillus*, the vectors include pUB110 plasmid and pC194 plasmid. Integration into chromosome is also possible. The promoters and terminators that can be utilized include promoters and terminators of genes of enzymes such as alkaline protease, neutral protease, and α-amylase.

In the case of *Pseudomonas*, the vectors include commonly used host vector systems established for *Pseudomonas putida, Pseudomonas cepacia*, and so on, a broad host range vector (containing a gene necessary for autonomic replication derived from, for example, RSF1010) pKT240 based on TOL plasmid that participates in decomposition of toluene compounds (Gene, 26, 273-82 (1983)).

In the case of *Brevibacterium*, particularly *Brevibacterium lactofermentum*, the vectors include plasmid vectors such as pAJ43 (Gene, 39, 281 (1985)). The promoters and terminators that can be used include various promoters and terminators used for *Escherichia coli*.

In the case of *Corynebacterium*, particularly *Corynebacterium glutamicum*, the vectors include plasmid vectors such as pCS11 (JP 57-183799 A) and pCB101 (Mol. Gen. Genet. 196, 175 (1984).

In the case of *Saccharomyces*, particularly *Saccharomyces cerevisiae*, the vectors include plasmids such as YRp, YEp, YCp, and YIp plasmids. Promoters and terminators of genes of various enzymes such as alcohol dehydrogenase, glyceryl aldehyde-3-phosphate dehydrogenase, acidic phosphatase, β-galactosidase, phosphoglycerate kinase, and enolase can also be used.

In the case of *Schizosaccaromyces*, the vectors include plasmid vectors derived from *Schizosaccharomyces pombe* described in Mol. Cell. Biol. 6, 80 (1986). In particular, pAUR224 is commercially available from Takara Shuzo and can be readily used.

In the case of *Aspergillus, Aspergillus niger, Aspergillus orizae*, and so on have been best studied among molds and integration into a plasmid and chromosome can be used, and promoters derived from extracellular protease or amylase can be used (Trends in Biotechnology 7, 283-287 (1989)).

Further, besides those described above, host vector systems depending on various microbials have been established and they can be used appropriately. In addition, various host vector systems have been established in plants and animals in addition to the microbials. In particular, systems that allow hetero proteins to be expressed in large amounts in animals, particularly insects such as a silkworm (Nature 315, 592-594 (1985)) and in plants such as rapeseed, corn, and potato, as well as systems using cell-free protein synthesizing systems such as *Escherichia coli* cell-free extract solution and wheat germ have been established and can be used appropriately.

Further, the present invention relates to a process for producing an optically active alcohol by reacting the transformant cells of the present invention obtained by the above-mentioned method or the like, culture broth of the transformant cells, or treated products of the transformant cells with a compound represented by one of the general formulae (I), (II), and (III) as a reaction substrate to cause an asymmetric reduction of the carbonyl group of the compound. The transformant cells, culture broth of the transformant cells, and treated products of the transformant cells may be used singly or in combination.

A compound represented by the following formula (I)

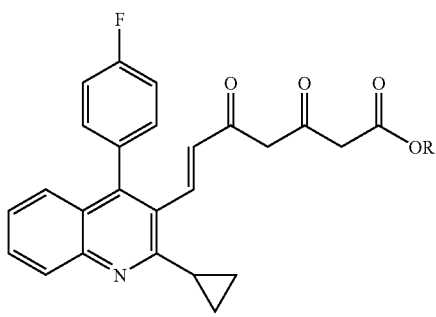

I (where R represents a hydrogen atom, an alkyl group, or an aryl group);

A compound represented by the following formula (II)

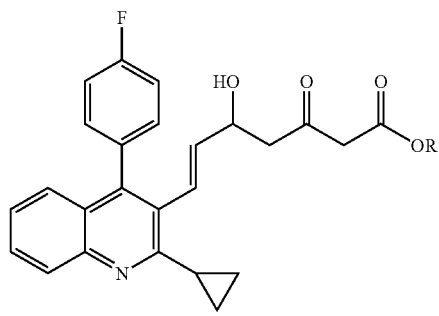

II (where R has the same meaning as that described above); and

A compound represented by the following formula (III)

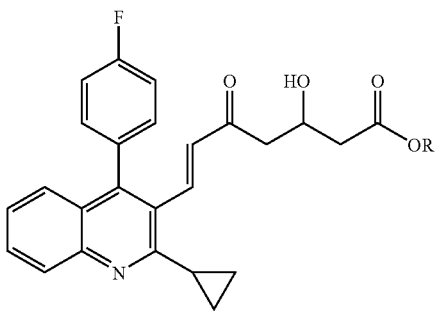

III (where R has the same meaning as that described above).

In the compounds represented by the above formulae (I) to (III), which are raw materials to be used in the production process of the present invention, R represents a hydrogen atom, an alkyl group, or an aryl group.

Examples of the alkyl group include: a straight-, branched-, or cyclic alkyl group which may be substituted with an alkyl group or an aryl group, such as a methyl group, an ethyl group, an isopropyl group, a cyclopropyl group, a butyl group, an isobutyl group, a t-butyl group, a cyclohexyl group, a benzyl group, or a phenethyl group.

Examples of the aryl group include a phenyl group or a naphthyl group which may be substituted with an alkyl group, such as a phenyl group, a mesityl group, or a naphthyl group.

The above R is preferably a $C_1$-$C_4$ alkyl group, a benzyl group, or a phenyl group, more preferably a $C_1$-$C_4$ alkyl group, particularly preferably a methyl group or an ethyl group.

In the production process of the present invention, the compounds represented by the formulae (II) and (III) contain at least optically active forms represented by the following formulae (II') and (III'), respectively. It is preferable that among the compounds represented by the formulae (II) and (III), the contents of the compounds represented by the formulae (II') and (III') be large. Further, it is preferable that the compounds represented by the formulae (II) and (III) consist of those represented by the formulae (II') and (III'). For the compounds represented by the formulae (II') and (III'), R has the same meaning as that described above.

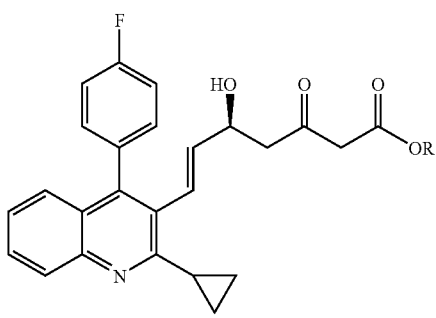

II'

(where R has the same meaning as that described above)

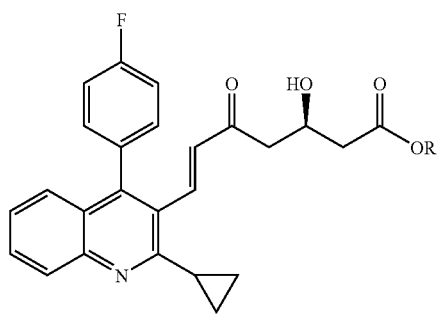

III'

(where R has the same meaning as that described above)

Note that the products obtained from the compounds represented by the formulae (I) to (III) and (II') and (III') according to the production process of the present invention may be mixtures but contain at least the compounds represented by the following formula (IV). In the compounds represented by the following formula (IV), R has the same meaning as that described above.

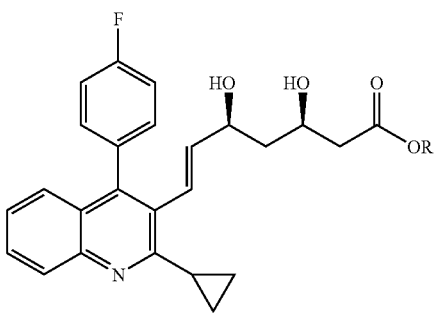

IV (where R has the same meaning as that described above).

The compounds represented by the formulae (I) to (III) and (II') and (III') can be optionally produced with a combination of a process disclosed in JP 1-279866 A, JP 8-127585 A, JP 5-178841 A, or the like and a process well known in the art. Those compounds may be used singly or two or more may be combined and used as the raw materials.

In the case where a compound represented by the formula (IV) is produced by using a compound represented by the formula (I) as a raw material, there are two routes, i.e., a route in which production is performed through a compound represented by the formula (II') as an intermediate product and a route in which production is performed through a compound represented by the formula (III') as an intermediate product.

The compound represented by the formula (II') and the compound represented by the formula (III') may be prepared in advance from the compound represented by the formula (I), isolated, and further derived into the compound represented by the formula (IV). Alternatively, the compound represented by the formula (II') and the compound represented by the formula (III') may be used as they are without isolation directly for producing the compound represented by the formula (IV).

Further, the reaction substrate is used at a substrate concentration of usually in the range of 0.01 to 90 w/v %, preferably 0.1 to 30 w/v %. The reaction substrate may be added at a time upon initiation of the reaction. However, from the viewpoints of reducing the possible influence of substrate inhibition of the enzyme and of increasing accumulation concentration of the product, it is desirable to add continuously or intermittently.

In the production process of the present invention, when the above-mentioned transformant is acted on the carbonyl group-containing compound, the transformant cells themselves, culture broth of the transformant, or treated transformant cells obtained by treating the transformant cells by a known method, for example, treated bacterial cells such as one obtained by treating the transformant cells with organic solvents such as acetone, dimethyl sulfoxide (DMSO), and toluene or surfactants, one obtained by freeze-drying, one obtained by physically or enzymatically disrupting the transformant cells, one obtained by extracting the enzyme fraction of the present invention in the transformant cells as a crude purified product or purified product, and further one obtained by immobilizing these to a carrier typified by polyacrylamide gel or carrageenan can be used.

Further, in the production process of the present invention, it is preferable that coenzyme $NADP^+$ or NADPH be added. Usually, the coenzyme $NADP^+$ or NADPH is added in an amount of 0.001 mM to 100 mM, preferably 0.01 to 10 mM.

When the above-mentioned coenzyme is added, it is preferable that $NADP^+$ produced from NADPH be regenerated to NADPH in order to increase production efficiency. The regeneration method includes: 1) a method that utilizes $NADP^+$ reducing ability of host microbial itself; 2) a method including addition of a microbial having the ability of producing NADPH from $NADP^+$ or a treated product thereof or enzymes that can be used for regeneration of NADPH (regeneration enzymes) including glucose dehydrogenase, formic acid dehydrogenase, alcohol dehydrogenase, amino acid dehydrogenase, and organic acid dehydrogenase (such as malic acid dehydrogenase) into the reaction system; and 3) a method that includes incorporation of gene of the above-mentioned regeneration enzymes, which can be used for regeneration of NADPH, at the same time along with the DNA of the present invention into the host when the transformant is prepared.

Among the methods, in the method of 1) above, it is preferable that glucose, ethanol, formic acid, or the like be added to the reaction system.

Further, in the method of 2) above, microbial containing the above-mentioned regeneration enzymes, treated bacterial cell such as one obtained by treating the bacterial cell with acetone, one obtained by freeze-drying the bacterial cell, one obtained by physically or enzymatically disrupting bacterial cell, one obtained by extracting the enzyme fraction as a crude product or purified product, and, further, one obtained by immobilizing these to a carrier typified by polyacrylamide gel or carrageenan gel may be used. Alternatively, commercially available enzymes may be used.

In this case, the above-mentioned enzyme, specifically, is added in such an amount that the amount of the regeneration enzyme is about 0.01 to 100 folds, preferably about 0.5 to 20 folds the amount of the carbonyl reductase of the present invention.

Further, it becomes necessary to add the compound that can be used as a substrate of the above-mentioned regeneration enzyme, for example, glucose in the case where glucose dehydrogenase is used, formic acid in the case where formic acid dehydrogenase is used, or ethanol or isopropanol in the case where alcohol dehydrogenase is used. The substrate compound is added in an amount of 0.1 to 20 fold molar equivalent, preferably 1 to 5 fold molar equivalent with respect to the carbonyl group-containing compound being used as a reaction raw material.

Further, in the method of 3) above, a method that includes incorporating the DNA of the present invention and the DNA encoding the above-mentioned regeneration enzyme in a chromosome, a method that includes incorporating both the DNAs in a single vector and transforming the host therewith, and a method that includes incorporating the DNAs into separate vectors and thereafter transforming the host with the vectors may be used. In the case of the method that includes incorporating the DNAs into separate vectors and then transforming the host therewith, it is necessary to select vectors taking into consideration incompatibility between both the vectors.

In the case where a plurality of genes are incorporated into a single vector, it is possible to use a method that includes connecting regions that participate in control of expression, such as a promoter and a terminator to each gene and a method that includes expressing an operon containing a plurality of cistrons, such as lactose operon.

The production process of the present invention is performed in an aqueous solvent that contains a reaction substrate, the transformant cells of the present invention, culture broth of the transformant cells, or treated transformant, and various coenzymes added as necessary as well as a regeneration system for the coenzymes, or in a mixture of the aqueous solvent and an organic solvent. Buffers using sodium phosphate, potassium phosphate, and so on can be used as the above-mentioned aqueous solvent, in which optional components used in ordinary enzyme reactions, such as organic solvents and surfactants, are added appropriately. The organic solvents include: water-soluble solvents such as dimethyl sulfoxide (DMSO) and tetrahydrofuran (THF); and water-insoluble organic solvents such as butyl acetate and hexane. Those having high solubilities of reaction substrates are preferably used. The surfactants include Tween 80 and sugar esters.

The process of the present invention can be performed usually at a reaction temperature of 4 to 60° C., preferably 10 to 45° C. and usually at pH 3 to 11, preferably pH 5 to 8. It is also possible to perform the process by using a membrane reactor or the like.

The ester represented by the formula (IV)[(3R,5S)-(E)-7-[2-cyclopropyl-4-(4-fluorophenyl)-quinolin-3-yl]-3,5-dihydroxyhept-6-enoic acid ester] which is produced by the method of the present invention can be deesterified, and then be formed into a pharmaceutically accepted salt thereof.

The pharmaceutically accepted salts include, for example, inorganic salt such as sodium salt, potassium salt, magnesium salt, calcium salt and so on; organic amine salt such as ammonium salt, trimethylamine salt, diethylamine salt, piperazine salt, morpholine salt, piperidine salt, or amine salt, dioramine salt, tromethamine salt or the like. In the above-mentioned salts, calcium salt is preferable. As to cations such as magnesium, calcium or the like, they form salts with (3R,5S)-(E)-7-[2-cyclopropyl-4-(4-fluorophenyl]-quinolin-3-yl]-3,5-dihydroxyhept-6-enoic acid as divalent cations. Specifically, it is comprised (3R, 5S)-(E)-7-[2-cyclopropyl-4-(4-fluorophenyl]-quinolin-3-yl]-3,5-dihydroxyhept-6-enoic acid and magnesium ions, calcium ions or the like in the composition of 2:1 in the magnesium salt, calcium salt or the like thereof.

Further, the present invention also includes the method for producing the salts of the above-mentioned compound. Conversion from the compound represented by the formula (IV) to the salts thereof can be performed by the conventional methods. For example, the compound represented by the formula (IV) can be converted to a free acid form by hydrolyzing that at 0° C. to 100° C., preferably 10° C. to 70° C. in a mixture solvent of methanol, ethanol or the like and water, using an equimolar amount of bases, preferably lithium hydroxide, potassium hydroxide, sodium hydroxide or the like. The obtained free acid form can be formed into the compound represented by the formula (V), (3R,5S)-(E)-7-[2-cyclopropyl-4-(4-fluorophenyl]-quinolin-3-yl]-3,5-dihydroxyhept-6-enoic acid 1/2 calcium salt, for example, by reacting appropriate bases such as potassium hydroxide therewith (See U.S. Pat. No. 6,162,798).

The optically active alcohols produced by the process of the present invention can be purified by: separating the bacterial cells or protein in the reaction mixture after completion of the reaction by centrifugation, membrane treatment, or the like; and subjecting the resultant to a combination of extraction with an organic solvent such as ethyl acetate or toluene, distillation, column chromatography, crystallization, and so on appropriately.

EXAMPLES

Hereinafter, the present invention will be described in more detail based on examples. However, general modifications are allowed in the technical field of the present invention without departing from the gist of the present invention.

In the meantime, (E)-7-[2-cyclopropyl-4-(4-fluorophenyl)-quinolin-3-yl]-3,5-dihydroxyhept-6-enoic acid esters have isomers: (3S, 5R)-isomer, (3R, 5R)-isomer, and (3S, 5S)-isomer, in addition to the objective (3R, 5S)-isomer. As an example of (E)-7-[2-cyclopropyl-4-(4-fluorophenyl)-quinolin-3-yl]-3,5-dihydroxyhept-6-enoic acid esters (hereinafter, abbreviated as "DOLE"), the structural formula is as follows.

3S, 5R-DOLE and 3R, 5S-DOLE are syn-isomers of DOLE, and 3S, 5S-DOLE and 3R, 5R-DOLE are anti-isomers of DOLE.

In the examples, the purity of the (3R, 5S)-isomer which is the objective product is expressed by the excess enantiomer ratio. Specifically, the excess enantiomer ratio is represented by ((3R, 5S)-isomer−(3S, 5R)-isomer)/((3R, 5S)-isomer+(3S, 5R)-isomer) (% e.e).

Syn-DOLE

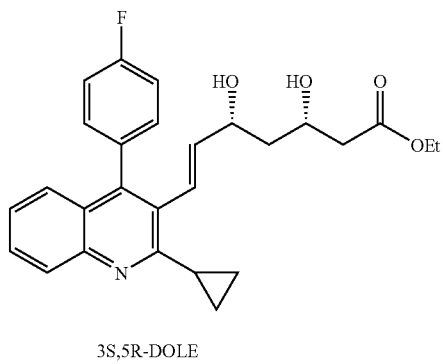

3S,5R-DOLE

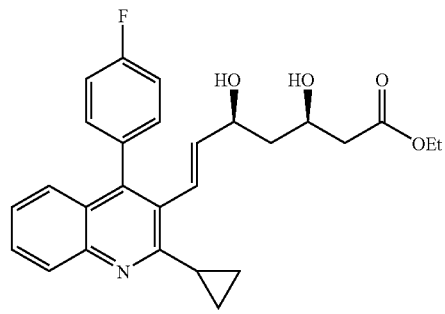

3R,5S-DOLE anti-DOLE

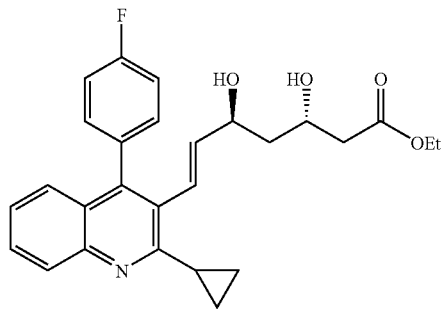

3S,5S-DOLE

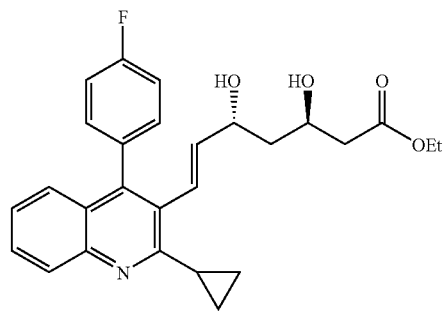

3R,5R-DOLE

Production Example 1

Synthesis of (E)-7-[2-cyclopropyl-4-(4-fluorophenyl)-quinolin-3-yl]-3,5-dioxohept-6-enoic acid ethyl ester (hereinafter, abbreviated as DOXE)

In a 500-ml four-neck flask equipped with a stirrer, a dropping funnel, and a thermo-meter, 5.02 g (11.22 mmol) of (E)-7-[2-cyclopropyl-4-(4-fluorophenyl)-quinolin-3-yl]-5-hydroxy-3-oxohept-6-enoic acid ethyl ester (hereinafter, abbreviated as 5-MOLE) and 420 mL of acetone were added and stirred. Then, 10.5 mL of a prepared Jones oxidizing agent (i.e., a reagent obtained by mixing 3 mL of a concentrated sulfuric acid and 3.35 g of chromium oxide together, followed by diluting up to 25 mL with water) was dropped at 0° C. in 20 minutes, and was then stirred under ice cooling for 2 hours, followed by gradually adding 10 mL of methanol to terminate the reaction. Subsequently, a reaction mixture solution was placed at reduced pressure to allow acetone to be distilled off, followed by the addition of 250 mL of ethyl acetate. The resulting solution was washed twice with 60 mL of saturated sodium bicarbonate aqueous solution, and was then washed twice with 60 mL of a brine to be extracted and separated, followed by drying an ethyl acetate solution with anhydrous magnesium sulfate. Subsequently, the solvent was distilled off, and purification was performed using a silica gel column chromatography (an eluting solvent; hexane:ethyl acetate=2:1), resulting in 3.03 g of an entitled compound (yield rate: 60.6%).

$^1$H-NMR (300 MHz, CDCl$_3$, δppm): 7.79-7.19 (8H, m), 7.71 (1H, d), 6.03 (1H, d), 5.51 (1H, s), 4.21 (2H, q), 3.40 (2H, s), 2.35-2.40 (1H, m), 1.39-1.41 (2H, m), 1.28 (3H, t), 1.07-1.09 (2H, m).

Production Example 2

Synthesis of 5S-(E)-7-[2-cyclopropyl-4-(4-fluorophenyl)-quinolin-3-yl]-5-hydroxy-3-oxo-hept-6-enoic acid ethyl ester (hereinafter, abbreviated as 5S-MOLE)

In a Schlenk tube introduced with nitrogen gas after being heated and dried at a reduced pressure, 0.87 g (3.3 mmol) of (S)-2-[N-(3-methyl-5-tert-butyl salicylidene) amino]-3-methyl-1-butanol, 5 ml of methylene chloride, and 0.63 ml (6.0 mmol) of titanium tetraethoxide were added, and stirred and mixed at room temperature for 1 hour. After cooling the Schlenk tube down to −50° C., 0.95 g (3.0 mmol) of (E)-3-[2-cyclopropyl-4-(4-fluorophenyl)-quinolin-3-yl]-prop-2-en-1-al dissolved in 2 ml of methylene chloride was dropped. After stirring the resultant for 5 minutes, 0.51 g (6 mmol) of diketene was further added, and stirred for 22 hours while keeping the temperature at −50° C. for the reaction. The resulting reaction mixture solution was added in a mixture solution of 25 ml of methylene chloride and 25 ml of a 0.24M sodium bicarbonate aqueous solution, and was vigorously stirred for 2 hours at room temperature to obtain a two-layer solution. The resulting two-layer solution was separated. A water layer was extracted twice with 10 ml of methylene chloride. The methylene chloride layer and the methylene chloride extract were combined together, resulting in a methylene chloride solution. The methylene chloride solution was dried with anhydrous magnesium sulfate and the solvent was distilled off, followed by purification with a silica gel column chromatography (an eluting solvent; hexane:ethyl acetate=3:2), resulting in 0.75 g of 5S-(E)-7-[2-cyclopropyl-4-(4-fluorophenyl)-quinolin-3-yl]-5-hydroxy- 3-oxo-hept-6-enoic acid ethyl ester (5S-MOLE) (optical purity: 73% e.e., and yield for (E)-3-[2-cyclopropyl-4-(4-fluorophenyl)-quinolin-3-yl]-prop-2-en-1-al: 56%).

Example 1

Isolation of Carbonyl Reductase

*Ogataea minuta* var. *nonfermentans* IFO 1473 strain was cultivated in 20 liters of YM medium (24 g glucose, 3 g yeast extract, 3 g malt extract, 5 g/l peptone, pH 6.0) and bacterial cells were prepared by centrifugation. 300 gout of the obtained wet bacterial cells were suspended in 50 mM potassium phosphate buffer (pH 7.0, 1 mM DTT) and disrupted in Dyno-Mill (manufactured by Dyno-Mill). Thereafter, the bacterial cell residue was removed by centrifugation to obtain a cell-free extract. 12-w/v % Polyethylene glycol (PEG) 6000 was added to the cell-free extract and the resultant was centrifuged to obtain a supernatant. The supernatant was added to DEAE-Sepharose 6FF (2.6 cm×28 cm) equilibrated with a standard buffer (10 mM potassium phosphate buffer (pH7.0), 1 nMDTT). After a column was washed with the standard buffer, it was further washed with a standard buffer that contains 0.07 M sodium chloride and then gradient elution with 0.07 to 0.18 M sodium chloride was performed. The eluted fractions were collected and measured for carbonyl reductase activity.

Carbonyl reductase activity was measured as to the following composition of reaction mixture, that is, 200 µl of an enzyme activity measuring fraction to which 10 µl of an aqueous solution of 0.1 mM potassium hydroxide containing 8 mM NADPH, 25 µl of 0.1 M phosphate buffer (pH 7.0), and 10 µl of 20 g/l DOXE (DMSO solution) were added, the reaction mixture was shaken overnight at 30° C. for reaction. The activity was detected by the following method. That is, 0.5 ml of ethyl acetate was added to the reaction mixture after completion of the reaction and vigorously mixed and separated into an organic layer and a water layer by centrifugation. The organic layer was transferred in another vessel and the solvent was distilled by a condensation centrifuge. The dried product was dissolved in 0.01 ml of ethyl acetate and thin layer chromatography (TLC) was performed. For the TLC, silica gel plate (Silica Gel 60 $F_{254}$ manufactured by Merck & Co.) was used and hexane/ethyl acetate=1/1 was used as development solvent. After completion of the development, the product was confirmed by using an UV lamp. The compound (I) had Rf=0.7 to 0.86, the compounds (II) and (III) had Rf=0.54 to 0.61, and the compound (IV) (wherein compound R=an ethyl group: DOLE) had Rf=0.33.

The activity of carbonyl reductase showed a peak in the vicinity of 0.13 M sodium chloride. The eluted active fractions were collected and ammonium sulfate was added thereto until a final concentration of 0.3 M was reached. Then, the resultant was added to octyl-Sepharose CL4B (0.8 cm×20 cm) equilibrated with a standard buffer (10 mM potassium phosphate buffer (pH7.0), 1 mM DTT) containing 0.3 M ammonium sulfate, and concentration gradient elution of 0.3 to 0 M of ammonium sulfate was performed. The activity of carbonyl reductase showed a peak in the vicinity of 0 M ammonium sulfate.

The eluted peak was collected and desalted to the concentration in the standard solution by ultrafiltration and concentrated. Thereafter, the resultant was added to MonoQ HR5/5 equilibrated with the same buffer and washed with the same buffer, and then with the same buffer but contains 0.05 M sodium chloride, followed by performing 0.05 M to 0.25 M sodium chloride concentration gradient elution. The active fraction of carbonyl reductase was eluted in 0.17 M sodium chloride fraction so that the fraction was collected and concentrated. The concentrated enzyme solution was subjected to gel filtration using Superdex 200 HR10/30 with the standard buffer containing 0.15 M sodium chloride. The active fraction obtained by the gel filtration had a molecular weight of about 107,000 Da.

Results of analysis of the above-mentioned active fraction on polyacrylamide gel electrophoresis (SDS-PAGE) indicated a substantially single band and the molecular weight thereof was about 27,000 Da.

Further, the reduction activity of the enzyme was measured by reacting the enzyme with various ketones and aldehyde, and measuring initial rate of NADPH decrease, specifically, in a reaction mixture that contains 5 µl of an isopropanol solution of 100 mm substrate, 10 µl of aqueous solution of 8 mM NADPH and 0.1 mM potassium hydroxide, and 0.1 M phosphate buffer (pH 7.0) to make a reaction mixture of a total volume of 250 µl. Table 1 shows specific activities of the enzyme assuming that a variation of optical absorption in 2,2,2-trifluoroacetophenone is defined as 100.

TABLE 1

| Substrate | Specific activity (%) |
| --- | --- |
| o-Nitrobenzaldehyde | 52.6 |
| m-Nitrobenzaldehyde | 45.6 |
| o-Chlorobenzaldehyde | 81.2 |
| m-Chlorobenzaldehyde | 14.3 |
| p-Chlorobenzaldehyde | 15.2 |
| Diacetyl | 12.3 |
| 2,3-Pentadione | 21.5 |
| 3-Chloro-2,4-pentadione | 32.7 |
| 1-Bromo-3,3-dimethyl-2-butanone | 55.4 |
| Ethyl-3-methyl-2-oxobutanoate | 72.1 |
| α-Keto-pantolactone | 26.3 |
| 2-Chloro-cyclohexanone | 163.0 |
| 2-Chloro-2-Methyl-cyclohexanone | 105.4 |
| Propiophenone | 18.8 |
| Benzylacetonitrile | 25.9 |
| Ethyl benzoylacetate | 10.9 |
| m-Chloro-acetophenone | 30.7 |
| p-Chloro-acetophenone | 10.2 |
| m-Bromo-acetophenone | 21.3 |
| 2-Chloro-acetophenone | 19.6 |
| 2,2,2-Trifluoro-acetophenone | 100.0 |

The optimum pH of the enzyme was determined by measuring 2,2,2-trifluoroacetophenone reducing activity in a plurality of buffers differing in pH from each other. Specifically, 0.1 M potassium buffers, sodium acetate buffers, and citrate buffers each differing in pH were prepared and activities were measured. The optimum pH of the reaction was 5.0 to 6.5.

Further, only the reaction temperature was varied and 2,2,2-trifluoroacetophenone reducing activity was measured to measure the optimum temperature of the action of the carbonyl reductase. As a result, the optimum temperature was 60 to 70° C.

The pH stability of the enzyme was examined by preparing a plurality of potassium phosphate buffers, sodium acetate buffers, and citrate buffers differing in pH and incubating each of them for 30 minutes at 30° C. to measure the residual activity. As a result, the highest stability was confirmed at pH 5.5 to 6.5.

The temperature stability of the enzyme was examined by allowing to stand in 20 mM phosphate buffer at pH7.0 at temperatures of 30° C., 40° C., 50° C., 60° C., 70° C., and 80° C. for 10 minutes and measuring 2,2,2-trifluoroacetophenone reducing activity. The results indicated that the enzyme of the present invention showed a residual activity of 79% or more up to 40° C. and rapidly deactivated at 50° C. or more, and lost the activity completely at 70° C.

Further, the enzyme was treated in various reagents at 30° C. for 10 minutes and then 2,2,2-trifluoroacetophenone reducing activity was measured. As a result, the activity of enzyme was considerably inhibited in the presence of mercury (I) ion or lead (II) ion such as mercury nitrate and lead chloride.

Example 2

Analysis of Partial Amino Acid Sequence of Carbonyl Reductase

The fraction containing the carbonyl reductase obtained in Example 1 was desalted, concentrated and then treated with lysylendopeptidase at 30° C. overnight. The digested peptide was subjected to acetonitrile gradient elution in 0.1% trifluoroacetic acid (TFA) using reversed-phase HPLC (URPC C2/C18 manufactured by Amersham-Pharmacia, 46 mm×100 mm) to resolve and fractionate a peptide. Three fractionated peptide peaks were named Frac20, 27, and 30 and each of them was analyzed for amino acid sequence by the Edman method. The respective amino acid sequences of Frac20, 27, and 30 are shown in SEQ ID NOs: 3, 4, and 5. Similarly, the fraction containing the carbonyl reductase was analyzed for N-terminal amino acid by the Edman method after desalting and the result is shown in SEQ ID NO: 6.

Example 3

Sequence Analysis of the DNA of the Present Invention Derived From *Ogataea minuta* var. *nonfermentans* IFO 1473 Strain and Making of Transformant

*Ogataea minuta* var. *nonfermentans* IFO 1473 strain was cultivated in YM medium and the bacterial cell thereof was prepared.

Purification of total RNA from the bacterial cells was performed using Mag Extractor (manufactured by Toyobo). First-Strand cDNA was synthesized based on the purified RNA using SuperScriptII (manufactured by Life Technology). The method was performed according to the attached manual.

Four kinds in total of primers, i.e., a sense degenerate primer based on the N-terminal amino acid sequence obtained in Example 2, and antisense degenerate primers based on SEQ ID NOs: 3, 4, and 5, respectively, were synthesized. The nucleotide sequences are shown in SEQ ID NOs: 7, 8, 9, and 10, respectively. Primers were selected based on the combinations (three types) of N-terminal and three partial amino acid sequences and PCR was performed using 50 μl of a reaction mixture containing each 400 pmol of primer, 0.4 mmol dNTP, 1 μl of cDNAs of *Ogataea minuta* var. *nonfermentans* IFO 1473 strain, 5 μl of 10× buffer for TaKaRaTaq (Manufactured by Takara Shuzo), and 2 units of heat-resistant DNA polymerase (trade name "TaKaRa Taq", manufactured by Takara Shuzo), by conducting 30 cycles of denaturation (94° C., 30 seconds), anneal (50° C., 30 seconds), and elongation (72° C., 1 minute) by means of RTC-200 Peltier Thermal Cycler (manufactured by MJ Research). Analysis of a part of the PCR reaction mixture by agarose gel electrophoresis indicated that bands considered to be specific were detected in the combination of the primer described in SEQ ID NO: 7 and the primer described in SEQ ID NO: 8, in the combination of the primer described in SEQ ID NO: 7 and the primer described in SEQ ID NO: 9, and in the combination of the primer described in SEQ ID NO: 7 and the primer described in SEQ ID NO: 10.

The three kinds of DNA fragments obtained as described above were subjected to agarose gel electrophoresis and objective bands were cut out, purified by a Gel Extraction kit (manufactured by QIAGEN) and recovered. The obtained DNA fragments were subjected to TA cloning by a pGEM-T Vector System (manufactured by Promega) and used for transforming Escherichia coli DH5α strain (manufactured by Toyobo). The transformants were grown on a medium plate containing 1% bactotriptone, 0.5% bacto yeast extract and 1% sodium chloride (hereinafter, referred to as "LB medium") to which ampicillin (100 μg/ml) was added and the medium was converted to the plate by addition of 1.5% bacto agar. Using some colonies, colony direct PCR was performed with SEQ ID NOs: 11 and 12 synthesized based on the sequences of the vectors as primers and the size of the inserted fragment was confirmed. Colonies assumed to have the objective DNA fragment inserted therein were cultivated in liquid LB medium containing 100 μg/ml ampicillin and plasmids were purified by Mini-Prep (manufactured by QIAGEN). The plasmids obtained by using the combination of the primer described in SEQ ID NO: 7 and the primer described in SEQ ID NO: 8, in the combination of the primer described in SEQ ID NO: 7 and the primer described in SEQ ID NO: 9, and in the combination of the primer described in SEQ ID NO: 7 and the primer described in SEQ ID NO: 10 were named phir21-23, phir21-25, and phir21-27, respectively.

The nucleotide sequence of the inserted DNA was analyzed by the diterminator method using the purified plasmids. The nucleotide sequences of respective inserted fragment portions of phir21-23, phir21-25, and phir21-27 thus determined are shown in SEQ ID NOs: 13, 14, and 15, respectively.

Total RNAs prepared from *Ogataea minuta* var. *nonfermentans* IFO 1473 strain was subjected to the 5' RACE method and 3' RACE method using primers designed based on the above-mentioned nucleotide sequences.

The 5' RACE method was performed using the primers having nucleotide sequences described in SEQ ID NOs: 16 and 17 as gene specific primers (hereinafter, referred to as "GSPs") 1 and 2 in 5' RACE System for Rapid Amplification of cDNA Ends, ver2.0 (manufactured by Life Technology) and then the resultant was used as templates and the 5' RACE method was again performed using the primer having the nucleotide sequence described in SEQ ID NO: 18 as GSP.

The 3' RACE method was performed using the primer having the nucleotide sequence shown in SEQ ID NO:19 as GSP and also the 3' RACE System for Rapid Amplification of cDNA Ends (manufactured by Life technology). Note that each of the RACE methods was carried out based on the manual attached.

The obtained DNA fragments were subjected to TA cloning by a pGEM-T Vector System (manufactured by Promega) and used for transforming *Escherichia coli* DH5α strain (manufactured by Toyobo). The transformants were grown on an LB medium plate containing 100 μg/ml ampicillin. Using some colonies, colony direct PCR was performed with SEQ ID NOs: 11 and 12 synthesized based on the sequences of the vectors as primers and the size of the inserted fragment was confirmed. Colonies assumed to have the objective DNA fragment inserted therein were cultivated in liquid LB medium containing 100 µg/ml ampicillin and plasmids were purified by Mini-Prep (manufactured by QIAGEN) and then analyzed for DNA nucleotide sequence by the diterminator method.

ORF search was performed on the 5' upstream nucleotide sequence and 3' downstream nucleotide sequence of phir21-25 obtained in the 5' RACE and 3' RACE as well as DNA sequence prepared based on the nucleotide sequence information described in SEQ ID NO:14 using Genetyx (manufactured by Software Development Co., Ltd.). The DNA sequence of the present invention and the amino acid sequence of the protein encoded thereby were provisionally determined to be the nucleotide sequence and amino acid sequence shown in SEQ ID NO: 20.

Results of homology search of the above-mentioned polypeptide performed on DDBJ using the BLAST program with the amino acid sequence shown in SEQ ID NO: 20 indicated that among the known proteins, the one that showed the highest homology was the probable short chain dehydrogenase (T41540) of *Schizosaccharomyces pombe*, which showed 37.4% homology. Subsequently, the nucleotide sequence described in SEQ ID NO: 21 and the nucleotide sequence described in SEQ ID NO: 22 were synthesized as primers for cloning based on the sequence described in SEQ ID NO: 20, and PCR was performed using 50 µl of a reaction mixture containing 50 pmol of each primer, 200 nmol of DNTP, 1 µl of cDNA of *Ogataea minuta* var. *nonfermentans* IFO 1473 strain, 5 µl of 10× buffer for KOD-DNA polymerase (manufactured by Toyobo), 2.5 units of KOD-DNA polymerase (manufactured by Toyobo), by conducting 30 cycles of denaturation (96° C., 30 seconds), anneal (54° C., 30 seconds), and elongation (74° C., 1 minute) by means of RTC-200 Peltier Thermal Cycler (manufactured by MJ Research). Analysis of a part of the PCR reaction mixture by agarose gel electrophoresis indicated that bands considered to be specific could be detected.

The band detected as described above was recovered by using a QIAGEN Gel Extraction kit (manufactured by QIAGEN). The recovered DNA fragment was digested with restriction enzymes HindIII and EcoRI, and subjected to agarose gel electrophoresis. The objective band was cut out, purified again by using a QIAGEN Gel Extraction kit (manufactured by QIAGEN) and then recovered. The obtained DNA fragment was ligated to pKK223-3 (manufactured by Pharmacia) digested with EcoRI and HindIII using a Takara Ligation kit and *Escherichia coli* JM109 strain was transformed therewith.

The transformants were grown on an LB medium plate containing ampicillin (50 µg/ml). Using some colonies, colony direct PCR was performed with the primer having the nucleotide sequence described in SEQ ID NO: 23 and the primer having the nucleotide sequence described in SEQ ID NO: 24 synthesized based on the sequences of the vectors as primers and the size of the inserted fragment was confirmed. Transformants assumed to have the objective DNA fragment inserted therein were cultivated in liquid LB medium containing 50 µg/ml ampicillin and plasmids were purified by using Qiagen 500 (manufactured by QIAGEN) to obtain pKK223-30CR1.

Analysis of nucleotide sequence of the DNA inserted in the plasmid by the diterminator method indicated that the inserted DNA fragment had a nucleotide sequence consisting of a gene having the nucleotide sequence represented by SEQ ID NO: 2 that has 6 bases for cloning added to the 5' upstream thereof and double stop codon (TAGTAAT) derived from *Ogataea minuta* var. *nonfermentans* IFO 1473 strain and 6 bases for cloning added to the 3'-downstream thereof.

The nucleotide sequence of the DNA fragment inserted into pKK233-30CR1 is shown in SEQ ID NO: 25 and the amino acid sequence of the protein encoded by the DNA fragment is shown in SEQ ID NO: 1.

Example 5

Production of DOLE from DOXE Using *Escherichia coli* Transformed With the DNA of the Present Invention The transformant obtained in Example 4 was grown in LB medium containing ampicillin (50 µg/ml), 0.1 mm isopropyl β-D-thiogalactopyranoside (IPTG) at 37° C. for 17 hours and 2 ml of the obtained bacterial cell broth was centrifuged to collect the bacterial cells, which were suspended in 180 µl of 100 mM potassium phosphate buffer (pH 7.0). Thereafter, reducing activity of the transformant was confirmed by using (E)-7-[2-cyclopropyl-4-(4-fluorophenyl)-quinolin-3-yl]-3,5-dioxohept-6-enoic acid ethyl ester (DOXE) as a substrate.

After addition of 10 µl of 2 g/l NADP$^+$ (manufactured by Oriental Yeast) and 1 µl of toluene, the above-mentioned bacterial cell suspension was stirred with a vortex mixer for 5 minutes. After addition of 10 µl of 50% glucose, 10 µl of a glucose dehydrogenase solution (manufactured by Amano Pharmaceutical; 25 U/ml), and 50 µl of a 20 g/l DMSO solution of the above-mentioned substrate (corresponding to 1 mg of substrate), the mixture was shaken at 40° C. for 20 hours for reaction. After dilution of the reaction suspension after completion of the reaction by addition of 1.75 ml of acetonitrile, the resultant was centrifuged and the product in the supernatant was measured by using high performance liquid chromatography (HPLC). The conditions of HPLC were as follows.

Column: MCIGEL CHP2MGM (manufactured by Mitsubishi Chemical Corporation)
Eluting solution: Methanol/acetonitrile/water/phosphoric acid=800/100/100/1
Flow rate: 0.6 ml/min
Detection: UV 254 nm
Temperature: 60° C.

As a result, 319 µg yields and 31.9% yield rate were achieved.

Further, for measurement of the optical purity, after terminating the reaction, 0.5 mL of ethyl acetate was added in the reaction solution and was mixed therewith vigorously, followed by separation into anorganic layer and a water layer by a centrifugation. The organic layer was transferred to another vessel. A solvent was distilled off with a condensation centrifuge. Then, the dried product was dissolved in 0.01 mL of ethyl acetate, and was then subjected to thin layer chromatography (TLC). The TLC used was a silica gel plate (silica gel 60 $F_{254}$ manufactured by Merck & Co.), and development solvent used was of hexane/ethyl acetate=1/1.

After terminating the development, the product was confirmed with an UV lamp. As for the compound (I), Rf=0.76 to 0.86. As for compounds (II) and (III), Rf=0.54 to 0.61. As for the compound (IV) (wherein the compound R=ethyl group: hereinafter abbreviated as DOLE), Rf=0.33. A spot of the DOLE on the TLC was scraped and eluted with 0.25 mL of isopropanol. After the centrifugation, a supernatant was subjected to a high performance liquid chromatography (HPLC) to analyze its optical purity and the concentration of a TLC-scraped-off sample.

The following are the conditions of the HPLC.
Column: Daicel CHIRALCEL AD
Eluting solution: Hexane/ethanol/trifluoroacetate=900/100/1
Flow rate: 1 ml/min
Detection: UV 254 nm
Temperature: Room temperature This resulted in 100% e.e. optical purity, and 0.6% anti-isomer.

Further, bacterial cells of *Escherichia coli* having the plasmid pKK223-3 that did not contain the gene cultivated overnight in LB medium to which 0.1 mM IPTG was added was allowed to react in the same manner. However, the above-mentioned product was not detected.

Example 6

Production of DOLE From 5S-MOLE Using *Escherichia coli* Transformed With the DNA of the Present Invention The transformant obtained in Example 4 was grown in LB medium containing ampicillin (50 μg/ml), 0.1 mM isopropyl β-D-thiogalactopyranoside (IPTG) at 37° C. for 17 hours and 2 ml of the obtained bacterial cell broth was centrifuged to collect the bacterial cells, which were suspended in 180 μl of 100 mM potassium phosphate buffer (pH 7.0). Thereafter, reducing activity of the transformant was confirmed by using 5S-(E)-7-[2-cyclopropyl-4-(4-fluorophenyl)-quinolin-3-yl]-5-hydroxy-3-oxo-hept-6-enoic acid ethyl ester (5S-MOLE) as a substrate by the following method.

After addition of 10 μl of 2 g/l NADP$^+$ (manufactured by Oriental Yeast) and 1 μl of toluene, the above-mentioned bacterial cell suspension was stirred with a vortex mixer for 5 minutes. After addition of 10 μl of 50% glucose, 10 μl of a glucose dehydrogenase solution (manufactured by Amano Pharmaceutical; 25 U/ml), and 50 μl of a 20 g/l DMSO solution of the above-mentioned substrate (corresponding to 1 mg of substrate), the mixture was shaken at 40° C. for 20 hours for reaction. After dilution of the reaction suspension after completion of the reaction by addition of acetonitrile, the resultant was centrifuged and the product in the supernatant was measured by using high performance liquid chromatography (HPLC). The conditions of HPLC were as follows.
Column: Cosmosil 5C18MS-II, 4.6×250 mm (manufactured by Nacalai Tesque, Inc.)
Eluting solution: Methanol/acetonitrile/water/phosphoric acid=350/150/500/1
Flow rate: 0.6 ml/min
Detection: UV 254 nm
Temperature: 50° C.

This resulted in 807 μg yields, 80.7% yield rate, and 15.3% anti-isomer.

Further, for measurement of the optical purity, after terminating the reaction, 0.5 mL of ethyl acetate was added in the reaction solution and was mixed therewith vigorously, followed by separation into an organic layer and a water layer by a centrifugation. The organic layer was transferred to another vessel. A solvent was distilled off with a condensation centrifuge. Then, the dried product was dissolved in 0.01 mL of ethyl acetate, and was then subjected to thin layer chromatography (TLC). The TLC used was a silica gel plate (silica gel 60 $F_{254}$ manufactured by Merck & Co.), and development solvent used was of hexane/ethyl acetate=1/1.

After terminating the development, the product was confirmed with an UV lamp. As for the compound (I), Rf=0.76 to 0.86. As for compounds (II) and (III), Rf=0.54 to 0.61. As for the compound (IV) (wherein the compound R=ethyl group: hereinafter abbreviated as DOLE), Rf=0.33. A spot of the DOLE on the TLC was scraped and eluted with 0.25 mL of isopropanol. After the centrifugation, a supernatant was subjected to high performance liquid chromatography (HPLC) to analyze its optical purity and the concentration of a TLC-scraped-off sample.

The following are the conditions of the HPLC.
Column: Daicel CHIRALCEL AD
Eluting solution: Hexane/ethanol=95/5
Flow rate: 1 ml/min
Detection: UV 254 nm
Temperature: 50° C.

This resulted in 97% e.e. optical purity, and 15.2% anti-isomer.

Reaction of *Escherichia coli* having a plasmid pKK223-3 not containing the gene and an overnight cultivated bacterial cells with an LB medium having 0.1 mM IPTG added therein was attempted in the same way but the above-mentioned product was not recognized.

INDUSTRIAL APPLICABILITY

A production process that can provide optically active alcohols, which are industrially useful compounds as intermediate materials for drugs and pesticides, at high optical purity and in high yield is provided.

The invention claimed is:

1. An isolated DNA, consisting of a nucleotide sequence selected from the group consisting of:
   (a) a nucleotide sequence consisting of the nucleotide seguence encoding the polypeptide of SEQ ID NO: 1;
   (b) the nucleotide sequence of SEQ ID NO: 2; and
   (c) a nucleotide sequence that hybridizes with a nucleotide sequence complementary to SEQ ID NO: 2 under stringent conditions comprising washing with 0.1 X SSC solution at 65° C., and encodes a polypeptide having a caxbonyl reductase activity.

2. A recombinant DNA obtained by incorporating a DNA according to claim 1 into a vector.

3. A transformant having a recombinant DNA according to claim 2.

4. A transformant obtained by incorporating a DNA according to claim 1 into a chromosomal DNA.

* * * * *

SEQUENCE LISTING

<160> NUMBER OF SEQ ID NOS: 25

<210> SEQ ID NO 1
<211> LENGTH: 251
<212> TYPE: PRT
<213> ORGANISM: Ogataea minuta var nonfermentans

<400> SEQUENCE: 1

Met Ala Lys Thr Val Tyr Phe Ile Ala Gly Ala Ser Arg Gly Ile Gly
 1               5                  10                  15

Leu Glu Val Ala Ser Gln Leu Ser Ala Asn Pro Asp Asn Tyr Val Ile
            20                  25                  30

```
Ala Ser Tyr Arg Ser Glu Lys Ser Ala Ser Gly Leu Leu Glu Leu Ala
            35                  40                  45

Lys Lys Asp Asn Val Asp Thr Ile Val Leu Asp Ile Ala Ser Gln Glu
 50                  55                  60

Ser Ile Asp Ala Val Pro Ala Gln Ile Ser Lys Leu Thr Asp Gly Ile
 65                  70                  75                  80

Asp Val Ala Leu Ile Asn Ala Gly Ile Ala Asn Ala Met Cys Pro Ile
                 85                  90                  95

Leu Glu Cys Ser Arg Glu Ser Tyr Thr Asp His Trp Thr Thr Asn Ala
                100                 105                 110

Leu Gly Pro Ile Met Leu Tyr Gln Ala Ile His Lys Phe Met Leu Gln
            115                 120                 125

Arg Glu Thr Arg Lys Val Phe Phe Thr Thr Ser Ala Gly Gly Ser Ile
130                 135                 140

Gln Ala Lys Ile Pro Val Pro Val Ser Gly Tyr Gly Met Ser Lys Ala
145                 150                 155                 160

Ala Leu Asn Tyr Ala Val Arg Lys Leu Ala Asp Glu Cys Tyr Lys Asp
                165                 170                 175

Asn Phe Thr Ile Val Leu Leu His Pro Gly Phe Val Lys Thr Asp Met
            180                 185                 190

Gly Gln Ser Ala Ile Gln Lys Met Ser Asn Gly Asn Ala Glu Leu Leu
        195                 200                 205

Ala Tyr Ile Asp Ser Met Thr Ile Asp Val Pro Thr Ser Ala Gly Gln
    210                 215                 220

Ile Val Gly Ala Ile Met Thr Leu Asp Lys Gln Ser Ser Gly Arg Phe
225                 230                 235                 240

Ile Asn Ala Ala Asp Gln Phe Asp Met Pro Phe
                245                 250

<210> SEQ ID NO 2
<211> LENGTH: 753
<212> TYPE: DNA
<213> ORGANISM: Ogataea minuta var nonfermentans
<220> FEATURE:
<221> NAME/KEY: CDS
<222> LOCATION: (1)..(753)

<400> SEQUENCE: 2 atg gct aaa act gtt tac ttc atc gca ggt gct tcc aga ggt atc ggt      48
Met Ala Lys Thr Val Tyr Phe Ile Ala Gly Ala Ser Arg Gly Ile Gly
 1               5                  10                  15 ctc gag gtt gct tcc cag ctg agt gca aac cca gac aat tat gtt att      96
Leu Glu Val Ala Ser Gln Leu Ser Ala Asn Pro Asp Asn Tyr Val Ile
            20                  25                  30 gca tcc tat aga tct gaa aag tct gct tca gga ctt ttg gag ctg gca     144
Ala Ser Tyr Arg Ser Glu Lys Ser Ala Ser Gly Leu Leu Glu Leu Ala
        35                  40                  45 aag aag gat aat gtc gac aca att gtg ttg gat att gca agc cag gaa     192
Lys Lys Asp Asn Val Asp Thr Ile Val Leu Asp Ile Ala Ser Gln Glu
 50                  55                  60 tcg att gat gct gtt cca gca cag att tcc aag ctg act gat gga atc     240
Ser Ile Asp Ala Val Pro Ala Gln Ile Ser Lys Leu Thr Asp Gly Ile
 65                  70                  75                  80 gat gtt gcc ttg atc aac gct gga att gcc aac gct atg tgt ccg att     288
Asp Val Ala Leu Ile Asn Ala Gly Ile Ala Asn Ala Met Cys Pro Ile
                 85                  90                  95 ctc gaa tgt tct aga gag tcc tac act gat cac tgg aca acc aat gcc     336
Leu Glu Cys Ser Arg Glu Ser Tyr Thr Asp His Trp Thr Thr Asn Ala
```

```
                  100                 105                 110
ttg ggt cca atc atg ctc tac caa gct att cat aag ttc atg ctc cag      384
Leu Gly Pro Ile Met Leu Tyr Gln Ala Ile His Lys Phe Met Leu Gln
            115                 120                 125 aga gag acc aga aaa gtg ttc ttt acc acg agt gct ggt ggt tcc att      432
Arg Glu Thr Arg Lys Val Phe Phe Thr Thr Ser Ala Gly Gly Ser Ile
130                 135                 140 cag gct aag ata ccc gtg cct gtg agt ggt tac ggt atg tcc aag gct      480
Gln Ala Lys Ile Pro Val Pro Val Ser Gly Tyr Gly Met Ser Lys Ala
    145                 150                 155                 160 gcg ctt aat tat gct gtg aga aaa ctt gct gac gag tgc tac aag gac      528
Ala Leu Asn Tyr Ala Val Arg Lys Leu Ala Asp Glu Cys Tyr Lys Asp
                165                 170                 175 aac ttc act att gtg ttg ctg cat cct ggt ttt gtt aag acg gac atg      576
Asn Phe Thr Ile Val Leu Leu His Pro Gly Phe Val Lys Thr Asp Met
            180                 185                 190 ggt caa agc gcc att cag aag atg tca aat gga aat gct gag ctt ctt      624
Gly Gln Ser Ala Ile Gln Lys Met Ser Asn Gly Asn Ala Glu Leu Leu
        195                 200                 205 gct tac att gac tca atg act att gat gtt cct acc agt gct ggc caa      672
Ala Tyr Ile Asp Ser Met Thr Ile Asp Val Pro Thr Ser Ala Gly Gln
    210                 215                 220 atc gtc ggt gcc att atg acc ttg gac aag cag agc agc ggt aga ttt      720
Ile Val Gly Ala Ile Met Thr Leu Asp Lys Gln Ser Ser Gly Arg Phe
225                 230                 235                 240 atc aac gct gct gac cag ttt gac atg cca ttt                          753
Ile Asn Ala Ala Asp Gln Phe Asp Met Pro Phe
                245                 250

<210> SEQ ID NO 3
<211> LENGTH: 14
<212> TYPE: PRT
<213> ORGANISM: Ogataea minuta var nonfermentans

<400> SEQUENCE: 3

Val Phe Phe Thr Thr Ser Ala Gly Gly Ser Ile Gln Ala Lys
1               5                   10

<210> SEQ ID NO 4
<211> LENGTH: 16
<212> TYPE: PRT
<213> ORGANISM: Ogataea minuta var nonfermentans

<400> SEQUENCE: 4

Gln Ser Ser Gly Arg Phe Ile Asn Ala Ala Asp Gln Phe Asp Met Pro
1               5                   10                  15

<210> SEQ ID NO 5
<211> LENGTH: 13
<212> TYPE: PRT
<213> ORGANISM: Ogataea minuta var nonfermentans

<400> SEQUENCE: 5

Asp Asn Phe Thr Ile Val Leu Leu His Pro Gly Phe Val
1               5                   10

<210> SEQ ID NO 6
<211> LENGTH: 20
<212> TYPE: PRT
<213> ORGANISM: Ogataea minuta var nonfermentans

<400> SEQUENCE: 6
```

```
Ala Lys Thr Val Tyr Phe Ile Ala Gly Ala Ser Arg Gly Ile Gly Leu
 1               5                  10                  15
Glu Val Ala Ser
            20
```

<210> SEQ ID NO 7
<211> LENGTH: 26
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (3,9,12,24)
<223> OTHER INFORMATION: n=inosine

<400> SEQUENCE: 7
gcnaaracng tntayttyat hgcngg                                    26

<210> SEQ ID NO 8
<211> LENGTH: 29
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (4,13,16,19,22,25,28)
<223> OTHER INFORMATION: n=inosine

<400> SEQUENCE: 8
yttngcytgd atnswnccnc cngcnswng                                 29

<210> SEQ ID NO 9
<211> LENGTH: 32
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (1,19,22)
<223> OTHER INFORMATION: n=inosine

<400> SEQUENCE: 9
nggcatrtcr aaytgrtcng cngcrttdat ra                             32

<210> SEQ ID NO 10
<211> LENGTH: 33
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (1,7,10,16,19,22,28)
<223> OTHER INFORMATION: n=inosine

<400> SEQUENCE: 10
nacraanccn ggrtgnarna rnacdatngt raa                            33

<210> SEQ ID NO 11
<211> LENGTH: 19
<212> TYPE: DNA
<213> ORGANISM: Artificial Sequence
<220> FEATURE:
<223> OTHER INFORMATION: PCR primer

<400> SEQUENCE: 11

-continued

```
tatttaggtg acactatag                                              19

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
taatacgact cactataggg                                             20

<210> SEQ ID NO 13
<211> LENGTH: 438
<212> TYPE: DNA
<213> ORGANISM: Ogataea minuta var nonfermentans
<220> FEATURE:
<221> NAME/KEY: CDS
<222> LOCATION: (1)..(438)

<400> SEQUENCE: 13 gcg aaa acg gtg tat ttc atc gcg ggt gct tcc aga ggt atc ggt ctc    48
Ala Lys Thr Val Tyr Phe Ile Ala Gly Ala Ser Arg Gly Ile Gly Leu
  1               5                  10                  15 gag gtt gct tcc cag ctg agt gca aac cca gac aat tat gtt att gca    96
Glu Val Ala Ser Gln Leu Ser Ala Asn Pro Asp Asn Tyr Val Ile Ala
             20                  25                  30 tcc tat aga tct gaa aag tct gct tca gga ctt ttg gag ctg gca aag   144
Ser Tyr Arg Ser Glu Lys Ser Ala Ser Gly Leu Leu Glu Leu Ala Lys
         35                  40                  45 aag gat aat gtc gac aca att gtg ttg gat att gca agc cag gaa tcg   192
Lys Asp Asn Val Asp Thr Ile Val Leu Asp Ile Ala Ser Gln Glu Ser
     50                  55                  60 att gat gct gtt cca gca cag att tcc aag ctg act gat gga atc gat   240
Ile Asp Ala Val Pro Ala Gln Ile Ser Lys Leu Thr Asp Gly Ile Asp
 65                  70                  75                  80 gtt gcc ttg atc aac gct gga att gcc aac gct atg tgt ccg att ctc   288
Val Ala Leu Ile Asn Ala Gly Ile Ala Asn Ala Met Cys Pro Ile Leu
                 85                  90                  95 gaa tgt tct aga gag tcc tac act gat cac tgg aca acc aat gcc ttg   336
Glu Cys Ser Arg Glu Ser Tyr Thr Asp His Trp Thr Thr Asn Ala Leu
            100                 105                 110 ggt cca atc atg ctc tac caa gct att cat aag ttc atg ctc cag aga   384
Gly Pro Ile Met Leu Tyr Gln Ala Ile His Lys Phe Met Leu Gln Arg
        115                 120                 125 gag acc aga aaa gtg ttc ttt acc acc acc gcc ggc ggc acc att cag   432
Glu Thr Arg Lys Val Phe Phe Thr Thr Thr Ala Gly Gly Thr Ile Gln
    130                 135                 140 gcc aag                                                           438
Ala Lys
145

<210> SEQ ID NO 14
<211> LENGTH: 747
<212> TYPE: DNA
<213> ORGANISM: Ogataea minuta var nonfermentans
<220> FEATURE:
<221> NAME/KEY: CDS
<222> LOCATION: (1)..(747)

<400> SEQUENCE: 14 gcg aaa acg gtg tat ttc atc gcg ggt gct tcc aga ggt atc ggt ctc    48
Ala Lys Thr Val Tyr Phe Ile Ala Gly Ala Ser Arg Gly Ile Gly Leu
```

```
           1               5              10             15
gag gtt gct tcc cag ctg agt gca aac cca gac aat tat gtt att gca    96
Glu Val Ala Ser Gln Leu Ser Ala Asn Pro Asp Asn Tyr Val Ile Ala
                 20                  25                  30 tcc tat aga tct gaa aag tct gct tca gga ctt ttg gag ctg gca aag   144
Ser Tyr Arg Ser Glu Lys Ser Ala Ser Gly Leu Leu Glu Leu Ala Lys
             35                  40                  45 aag gat aat gtc gac aca att gtg ttg gat att gca agc cag gaa tcg   192
Lys Asp Asn Val Asp Thr Ile Val Leu Asp Ile Ala Ser Gln Glu Ser
 50                  55                  60 att gat gct gtt cca gca cag att tcc aag ctg act gat gga atc gat   240
Ile Asp Ala Val Pro Ala Gln Ile Ser Lys Leu Thr Asp Gly Ile Asp
 65                  70                  75                  80 gtt gcc tta atc aac gct gga att gcc aac gct atg tgt ccg att ctc   288
Val Ala Leu Ile Asn Ala Gly Ile Ala Asn Ala Met Cys Pro Ile Leu
                 85                  90                  95 gaa tgt tct aga gag tcc tac act gat cac tgg aca acc aat gcc ttg   336
Glu Cys Ser Arg Glu Ser Tyr Thr Asp His Trp Thr Thr Asn Ala Leu
            100                 105                 110 ggt cca atc atg ctc tac caa gct att cat aag ttc atg ctc cag aga   384
Gly Pro Ile Met Leu Tyr Gln Ala Ile His Lys Phe Met Leu Gln Arg
            115                 120                 125 gag acc aga aaa gtg ttc ttt acc acg agt gct ggt ggt tcc att cag   432
Glu Thr Arg Lys Val Phe Phe Thr Thr Ser Ala Gly Gly Ser Ile Gln
130                 135                 140 gct aag ata ccc gtg cct gtg agt ggt tac ggt atg tcc aag gct gcg   480
Ala Lys Ile Pro Val Pro Val Ser Gly Tyr Gly Met Ser Lys Ala Ala
145                 150                 155                 160 ctt aat tat gct gtg aga aaa ctt gct gac gag tgc tac aag gac aac   528
Leu Asn Tyr Ala Val Arg Lys Leu Ala Asp Glu Cys Tyr Lys Asp Asn
                165                 170                 175 ttc act att gtg ttg ctg cat cct ggt ttt gtt aag acg gac atg ggt   576
Phe Thr Ile Val Leu Leu His Pro Gly Phe Val Lys Thr Asp Met Gly
            180                 185                 190 caa agc gcc att cag aag atg tca aat gga aat gct gag ctt ctt gct   624
Gln Ser Ala Ile Gln Lys Met Ser Asn Gly Asn Ala Glu Leu Leu Ala
            195                 200                 205 tac att gac tca atg act att gat gtt cct acc agt gct ggc caa atc   672
Tyr Ile Asp Ser Met Thr Ile Asp Val Pro Thr Ser Ala Gly Gln Ile
            210                 215                 220 gtc ggt gcc att atg acc ttg gac aag cag agc agc ggt aga ttc atc   720
Val Gly Ala Ile Met Thr Leu Asp Lys Gln Ser Ser Gly Arg Phe Ile
225                 230                 235                 240 aac gcc gcc gac caa ttt gac atg ccc                               747
Asn Ala Ala Asp Gln Phe Asp Met Pro
                245

<210> SEQ ID NO 15
<211> LENGTH: 561
<212> TYPE: DNA
<213> ORGANISM: Ogataea minuta var nonfermentans
<220> FEATURE:
<221> NAME/KEY: CDS
<222> LOCATION: (1)..(561)

<400> SEQUENCE: 15 gcg aag acg gtg tac ttc atc gcg ggt gct tcc aga ggt atc ggt ctc    48
Ala Lys Thr Val Tyr Phe Ile Ala Gly Ala Ser Arg Gly Ile Gly Leu
 1               5                  10                  15 gag gtt gct tcc cag ctg agt gca aac cca gac aat tat gtt att gca    96
Glu Val Ala Ser Gln Leu Ser Ala Asn Pro Asp Asn Tyr Val Ile Ala
```

```
                20                  25                  30
tcc tat aga tct gaa aag tct gct tca gga ctt ttg gag ctg gca aag    144
Ser Tyr Arg Ser Glu Lys Ser Ala Ser Gly Leu Leu Glu Leu Ala Lys
        35                  40                  45 aag gat aat gtc gac aca att gtg ttg gat att gca agc cag gaa tcg    192
Lys Asp Asn Val Asp Thr Ile Val Leu Asp Ile Ala Ser Gln Glu Ser
 50                  55                  60 att gat gct gtt cca gca cag att tcc aag ctg act gat gga atc gat    240
Ile Asp Ala Val Pro Ala Gln Ile Ser Lys Leu Thr Asp Gly Ile Asp
 65                  70                  75                  80 gtt gcc ttg atc aac gct gga att gcc aac gct atg tgt ccg att ctc    288
Val Ala Leu Ile Asn Ala Gly Ile Ala Asn Ala Met Cys Pro Ile Leu
                85                  90                  95 gaa tgt tct aga gag tcc tac act gat cac tgg aca acc aat gcc ttg    336
Glu Cys Ser Arg Glu Ser Tyr Thr Asp His Trp Thr Thr Asn Ala Leu
            100                 105                 110 ggt cca atc atg ctc tac caa gct att cat aag ttc atg ctc cag aga    384
Gly Pro Ile Met Leu Tyr Gln Ala Ile His Lys Phe Met Leu Gln Arg
        115                 120                 125 gag acc aga aaa gtg ttc ttt acc acg agt gct ggt ggt tcc att cag    432
Glu Thr Arg Lys Val Phe Phe Thr Thr Ser Ala Gly Gly Ser Ile Gln
130                 135                 140 gct aag ata ccc gtg cct gtg agt ggt tac ggt atg tcc aag gct gcg    480
Ala Lys Ile Pro Val Pro Val Ser Gly Tyr Gly Met Ser Lys Ala Ala
145                 150                 155                 160 ctt aat tat gct gtg aga aaa ctt gct gac gag tgc tac aag gac aac    528
Leu Asn Tyr Ala Val Arg Lys Leu Ala Asp Glu Cys Tyr Lys Asp Asn
                165                 170                 175 ttc acc att gtc ctc ttc cac ccc ggc ttc gtc                        561
Phe Thr Ile Val Leu Phe His Pro Gly Phe Val
            180                 185

<210> SEQ ID NO 16
<211> LENGTH: 30
<212> TYPE: DNA
<213> ORGANISM: Artificial Sequence
<220> FEATURE:
<223> OTHER INFORMATION: PCR primer

<400> SEQUENCE: 16
agcagggccc ataacgttag caattcctgc                                    30

<210> SEQ ID NO 17
<211> LENGTH: 30
<212> TYPE: DNA
<213> ORGANISM: Artificial Sequence
<220> FEATURE:
<223> OTHER INFORMATION: PCR primer

<400> SEQUENCE: 17
gtgatgtcga tcccatccgt cagctgggag                                    30

<210> SEQ ID NO 18
<211> LENGTH: 30
<212> TYPE: DNA
<213> ORGANISM: Artificial Sequence
<220> FEATURE:
<223> OTHER INFORMATION: PCR primer

<400> SEQUENCE: 18
atttgggaac gcacccctc aattgactcc                                     30
```

<210> SEQ ID NO 19
<211> LENGTH: 24
<212> TYPE: DNA
<213> ORGANISM: Artificial Sequence
<220> FEATURE:
<223> OTHER INFORMATION: PCR primer

<400> SEQUENCE: 19
cttgctgacg agtgctacaa ggac                                         24

<210> SEQ ID NO 20
<211> LENGTH: 1158
<212> TYPE: DNA
<213> ORGANISM: Ogataea minuta var nonfermentans
<220> FEATURE:
<221> NAME/KEY: CDS
<222> LOCATION: (114)..(876)

<400> SEQUENCE: 20

```
aactccgtgt aagaattcag atctaggggc ctagaatttg aaatttcttg aaagatcgat      60
atgactgaaa tactataaaa gaagctgggt ttccgggtat atctcatagc atc atg       116
                                                          Met
                                                            1 gct aaa act gtt tac ttc att gct ggt gct tct aga ggt atc ggc ctc      164
Ala Lys Thr Val Tyr Phe Ile Ala Gly Ala Ser Arg Gly Ile Gly Leu
          5                  10                  15 gag gtt gcc acc caa ttg agt tcc aac cct gat aat tat gtt ata gga      212
Glu Val Ala Thr Gln Leu Ser Ser Asn Pro Asp Asn Tyr Val Ile Gly
     20                  25                  30 tcg tac aga tct aaa aag agc gct tcc gct cta atg gaa tta gcc aag      260
Ser Tyr Arg Ser Lys Lys Ser Ala Ser Ala Leu Met Glu Leu Ala Lys
 35                  40                  45 aag gaa aat gtg gat acg gtc att ctg gac att gcc agc cag gag tca      308
Lys Glu Asn Val Asp Thr Val Ile Leu Asp Ile Ala Ser Gln Glu Ser
 50                  55                  60                  65 att gag ggt gtg cgt tcc caa atc tcc cag ctg acg gat ggg atc gac      356
Ile Glu Gly Val Arg Ser Gln Ile Ser Gln Leu Thr Asp Gly Ile Asp
             70                  75                  80 atc aca ttg atc aat gca gga att gct aac gtt atg ggc cct gct gct      404
Ile Thr Leu Ile Asn Ala Gly Ile Ala Asn Val Met Gly Pro Ala Ala
         85                  90                  95 acc acc tct aga gaa gat tat gtt act cac tgg acc acc aat gct cta      452
Thr Thr Ser Arg Glu Asp Tyr Val Thr His Trp Thr Thr Asn Ala Leu
    100                 105                 110 ggt cca atc atg gtg tac aag gag atc cac gaa ttg atg ttg aag aag      500
Gly Pro Ile Met Val Tyr Lys Glu Ile His Glu Leu Met Leu Lys Lys
115                 120                 125 gat act aga aag gta ttc ttt act acg agt gct ggt ggt tcc att cag      548
Asp Thr Arg Lys Val Phe Phe Thr Thr Ser Ala Gly Gly Ser Ile Gln
130                 135                 140                 145 gct aag ata ccc gtg cct gtg agt ggt tac ggt atg tcc aag gct gcg      596
Ala Lys Ile Pro Val Pro Val Ser Gly Tyr Gly Met Ser Lys Ala Ala
                150                 155                 160 ctt aat tat gct gtg aga aaa ctt gct gac gag tgc tac aag gac aac      644
Leu Asn Tyr Ala Val Arg Lys Leu Ala Asp Glu Cys Tyr Lys Asp Asn
            165                 170                 175 ttc act att gtg ttg ctg cat cct ggt ttt gtt aag acg gac atg ggt      692
Phe Thr Ile Val Leu Leu His Pro Gly Phe Val Lys Thr Asp Met Gly
        180                 185                 190 caa agc gcc att cag aag atg tca aat gga aat gct gag ctt ctt gct      740
Gln Ser Ala Ile Gln Lys Met Ser Asn Gly Asn Ala Glu Leu Leu Ala
    195                 200                 205
```

```
tac att gac tca atg act att gat gtt cct acc agt gct ggc caa atc      788
Tyr Ile Asp Ser Met Thr Ile Asp Val Pro Thr Ser Ala Gly Gln Ile
210                 215                 220                 225 gtc ggt gcc att atg acc ttg gac aag cag agc agc ggt aga ttt atc      836
Val Gly Ala Ile Met Thr Leu Asp Lys Gln Ser Ser Gly Arg Phe Ile
                230                 235                 240 aac gct gct gac cag ttt gac atg cca ttt tag taa cgaagatcta gggatt    888
Asn Ala Ala Asp Gln Phe Asp Met Pro Phe
            245                 250 gagcagtcag caggagaatc gaacctcatt gcagatttca gacaagtaga ggctacgcta    948
atatggatca gttgtggatt ctctgctcgt ctctactctc ttcggcccta acttggagtt   1008
caggttcaga tttaacaaac ttatttcgat gaaggaaaag agacattgac taacataatt   1068
ccgaggccga taaaagtctt gatagcttga attacttact tattctatag aaataaaacg   1128
cctgcggtgt ggcaaaaaaa aaaaaaaaa                                     1158

<210> SEQ ID NO 21
<211> LENGTH: 31
<212> TYPE: DNA
<213> ORGANISM: Artificial Sequence
<220> FEATURE:
<223> OTHER INFORMATION: PCR primer

<400> SEQUENCE: 21
ggggaattca tggctaaaac tgtttacttc a                                    31

<210> SEQ ID NO 22
<211> LENGTH: 38
<212> TYPE: DNA
<213> ORGANISM: Artificial Sequence
<220> FEATURE:
<223> OTHER INFORMATION: PCR primer

<400> SEQUENCE: 22
ccccaagctt attactaaaa tggcatgtca aactggtc                             38

<210> SEQ ID NO 23
<211> LENGTH: 24
<212> TYPE: DNA
<213> ORGANISM: Artificial Sequence
<220> FEATURE:
<223> OTHER INFORMATION: PCR primer

<400> SEQUENCE: 23
gagcggataa caatttcaca cagg                                            24

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
cttctctcat ccgccaaaac                                                 20

<210> SEQ ID NO 25
<211> LENGTH: 772
<212> TYPE: DNA
<213> ORGANISM: Ogataea minuta var nonfermentans
<220> FEATURE:
<221> NAME/KEY: CDS
<222> LOCATION: (7)..(759)
```

<400> SEQUENCE: 25

```
gaattc atg gct aaa act gtt tac ttc atc gca ggt gct tcc aga ggt         48
       Met Ala Lys Thr Val Tyr Phe Ile Ala Gly Ala Ser Arg Gly
       1               5                   10 atc ggt ctc gag gtt gct tcc cag ctg agt gca aac cca gac aat tat         96
Ile Gly Leu Glu Val Ala Ser Gln Leu Ser Ala Asn Pro Asp Asn Tyr
15                  20                  25                  30 gtt att gca tcc tat aga tct gaa aag tct gct tca gga ctt ttg gag        144
Val Ile Ala Ser Tyr Arg Ser Glu Lys Ser Ala Ser Gly Leu Leu Glu
                35                  40                  45 ctg gca aag aag gat aat gtc gac aca att gtg ttg gat att gca agc        192
Leu Ala Lys Lys Asp Asn Val Asp Thr Ile Val Leu Asp Ile Ala Ser
            50                  55                  60 cag gaa tcg att gat gct gtt cca gca cag att tcc aag ctg act gat        240
Gln Glu Ser Ile Asp Ala Val Pro Ala Gln Ile Ser Lys Leu Thr Asp
65                  70                  75 gga atc gat gtt gcc ttg atc aac gct gga att gcc aac gct atg tgt        288
Gly Ile Asp Val Ala Leu Ile Asn Ala Gly Ile Ala Asn Ala Met Cys
        80                  85                  90 ccg att ctc gaa tgt tct aga gag tcc tac act gat cac tgg aca acc        336
Pro Ile Leu Glu Cys Ser Arg Glu Ser Tyr Thr Asp His Trp Thr Thr
95                  100                 105                 110 aat gcc ttg ggt cca atc atg ctc tac caa gct att cat aag ttc atg        384
Asn Ala Leu Gly Pro Ile Met Leu Tyr Gln Ala Ile His Lys Phe Met
                115                 120                 125 ctc cag aga gag acc aga aaa gtg ttc ttt acc acg agt gct ggt ggt        432
Leu Gln Arg Glu Thr Arg Lys Val Phe Phe Thr Thr Ser Ala Gly Gly
            130                 135                 140 tcc att cag gct aag ata ccc gtg cct gtg agt ggt tac ggt atg tcc        480
Ser Ile Gln Ala Lys Ile Pro Val Pro Val Ser Gly Tyr Gly Met Ser
145                 150                 155 aag gct gcg ctt aat tat gct gtg aga aaa ctt gct gac gag tgc tac        528
Lys Ala Ala Leu Asn Tyr Ala Val Arg Lys Leu Ala Asp Glu Cys Tyr
        160                 165                 170 aag gac aac ttc act att gtg ttg ctg cat cct ggt ttt gtt aag acg        576
Lys Asp Asn Phe Thr Ile Val Leu Leu His Pro Gly Phe Val Lys Thr
175                 180                 185                 190 gac atg ggt caa agc gcc att cag aag atg tca aat gga aat gct gag        624
Asp Met Gly Gln Ser Ala Ile Gln Lys Met Ser Asn Gly Asn Ala Glu
                195                 200                 205 ctt ctt gct tac att gac tca atg act att gat gtt cct acc agt gct        672
Leu Leu Ala Tyr Ile Asp Ser Met Thr Ile Asp Val Pro Thr Ser Ala
            210                 215                 220 ggc caa atc gtc ggt gcc att atg acc ttg gac aag cag agc agc ggt        720
Gly Gln Ile Val Gly Ala Ile Met Thr Leu Asp Lys Gln Ser Ser Gly
225                 230                 235 aga ttt atc aac gct gct gac cag ttt gac atg cca ttt tag taa taa        768
Arg Phe Ile Asn Ala Ala Asp Gln Phe Asp Met Pro Phe
        240                 245                 250 gctt                                                                   772
```